US010300093B2

(12) United States Patent
Pierce et al.

(10) Patent No.: US 10,300,093 B2
(45) Date of Patent: *May 28, 2019

(54) INHIBITING OR REDUCING FUNGAL INFECTIONS

(71) Applicant: GEORGIA STATE UNIVERSITY AND RESEARCH FOUNDATION, INC., Atlanta, GA (US)

(72) Inventors: George E. Pierce, Canton, GA (US); Sidney A. Crow, Jr., Smyrna, GA (US); Trudy Ann Tucker, Atlanta, GA (US); Christopher T. Cornelison, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 65 days.

This patent is subject to a terminal disclaimer.

(21) Appl. No.: 15/317,814

(22) PCT Filed: Jun. 10, 2015

(86) PCT No.: PCT/US2015/035146
§ 371 (c)(1),
(2) Date: Dec. 9, 2016

(87) PCT Pub. No.: WO2015/191744
PCT Pub. Date: Dec. 17, 2015

(65) Prior Publication Data
US 2017/0112882 A1    Apr. 27, 2017

Related U.S. Application Data

(60) Provisional application No. 62/010,295, filed on Jun. 10, 2014.

(51) Int. Cl.
*C12N 9/80* (2006.01)
*A61K 35/74* (2015.01)
*C02F 3/00* (2006.01)
*A01N 63/02* (2006.01)
*A01N 63/00* (2006.01)
*A61K 45/06* (2006.01)
*A61K 47/26* (2006.01)

(52) U.S. Cl.
CPC .............. *A61K 35/74* (2013.01); *A01N 63/00* (2013.01); *A01N 63/02* (2013.01); *A61K 45/06* (2013.01); *A61K 47/26* (2013.01)

(58) Field of Classification Search
CPC ... C12P 21/06; C12N 9/80; C12R 1/01; C02F 3/00
See application file for complete search history.

(56) References Cited

U.S. PATENT DOCUMENTS 7,531,343 B2   5/2009  Pierce et al.
7,531,344 B2   5/2009  Pierce et al.
7,943,549 B2   5/2011  Pierce et al.
2010/0210745 A1   8/2010  McDaniel et al.
2011/0274660 A1  11/2011  Jacobs et al.

FOREIGN PATENT DOCUMENTS

| EP | 0790310 | 8/1997 |
|---|---|---|
| JP | 54129190 | 10/1979 |
| JP | 2000470 | 1/1990 |
| JP | 5236977 | 9/1993 |
| JP | 8056684 | 3/1996 |
| JP | 8154691 | 6/1996 |
| JP | 8187092 | 7/1996 |
| WO | 2011091374 A2 | 7/2011 |
| WO | 2014159628 A2 | 10/2014 |
| WO | 2014160354 A1 | 10/2014 |

OTHER PUBLICATIONS

Kerr, "Suppression of Fungal Growth Exhibited by Pseudomonas aeruginosa", J of Clin Microbiol Feb. 1994, p. 525-527 (Year: 1994).*
International Preliminary Report on Patentability issued in PCT/US15/35146, dated Dec. 22, 2016.
International Search Report and Written Opinion issued in PCT/US15/35146, dated Sep. 30, 2015.
Abdel-Megeed, et al., "Biochemical Characterization of Antimicrobial Activity of Glycolipids produced by Rhodococcus Erythropolis", Pak. J. Bot. 43:2, 2011, 1323-1334.
Boyles, et al., "Economic Importance of Bats in Agriculture", Science 332, 2011, 41-42.
Bucke, et al., "Cell immobilization in calcium alginate", Methods in Enzymology 135, 1987, 175-189.
Collins, et al., "The Utilization of Nitriles and Amides by Nocardia rhodochrous", Journal of General Microbiology 129, 1983, 711-718.
Cortes-Sanchez, et al., "Biological activity of glycolipids produced by microorganisms: New trends and possible therapeutic alternatives", Microbiol. Research 168, 2013, 22-32.
Fawcett, et al., "A Rapid and Precise Method for the Determination of Urea", J. Clin. Pathol. 13, 1960, 156-159.
Giillam, et al., "Site-specific mutagenesis using synthetic oligodeoxyribonucleotide primers: I. Optimum conditions and minimum ologodeoxyribonucleotide length", Gene 8, 1979, 81-97.
Harper, "Characterization of a nitrilase from *Nocardia* sp. (Rhodochrous group) N.C.I.B. 11215, using p-hydroxybenzonitrile as sole carbon source." Int J Biochem. 17(6), 1985, 677-683.
Harper, "Microbial Metabolism of Aromatic Nitriles; Enzymology of C—N Cleavage by *Nocardia* Sp. (Rhodochrous Group) N.C.I.B. 11216", Harper Biochem. J. 165, 1977, 309-319.

(Continued)

*Primary Examiner* — Ruth A Davis
(74) *Attorney, Agent, or Firm* — Thomas|Horstemeyer, LLP

(57) ABSTRACT

Provided are methods and compositions for inhibiting or reducing fungal growth in or on a subject. The methods comprise exposing the subject to a composition comprising one or more enzymes, one or more bacteria, and/or an enzymatic extract, wherein the one or more enzymes, one or more bacteria, and/or the enzymatic extract isolated from one or more bacteria are exposed to the subject in a quantity sufficient to inhibit or reduce fungal growth.

22 Claims, 13 Drawing Sheets

(56) References Cited

OTHER PUBLICATIONS

Linton, et al.,"Utilization of Aliphatic Amides and Nitriles by Nocardia rhodochrous LL100-21" J Gen. Microbiol. 132, 1986, 1493-1501.

Lopez-Gallego, et al., "Enzyme stabilization by glutaraldehyde crosslinking of adsorbed proteins on aminated supports", J. Biotechnol. 119, 2005, 70-75.

Needleman, et al., "A General Method Applicable to the Search for Similarities in the Amino Acid Sequence of Two Proteins", J. Mol. Biol. 48, 1970, 443-453.

Rice, et al., "EMBOSS: The European Molecular Biology Open Software Suite", Trends Genet. 16, 2000, 276-7.

Roberts, et al., "Generation of an antibody with enhanced affinity and specificity for its antigen by protein engineering", Nature 328, 1987, 731-734.

Wang, "Enhanced Activity and Stability of Enzymes Associates wih Delayed Fruit Ripening in Rhodococcus rhodochrous DAP 96253", 2013, 132 pages.

Yamaki, et al., "Cloning and sequencing of a nitrile hydratase gene from Pseudonocardia thermophila JCM3095", J. Ferm. Bioeng. 83, 1997, 474-477.

Pierce et al., Preliminary report on a catalyst derived from induced cells of Rhodococcus rhodochrous strain DAP 96253 that delays the ripening of selected climacteric fruit: bananas, avocados, and peaches, J Ind Microbiol Biotechnol 38:1567-1573, 2011.

Wang, Enhanced Activity and Stability of Enzymes Associated with Delayed Fruit Ripening in Rhodococcus rhodochrous DAP 96253, Biology Dissertations, 2013.

Search Report issued by the European Patent office for Application 15806401.4, dated Oct. 23, 2017.

* cited by examiner

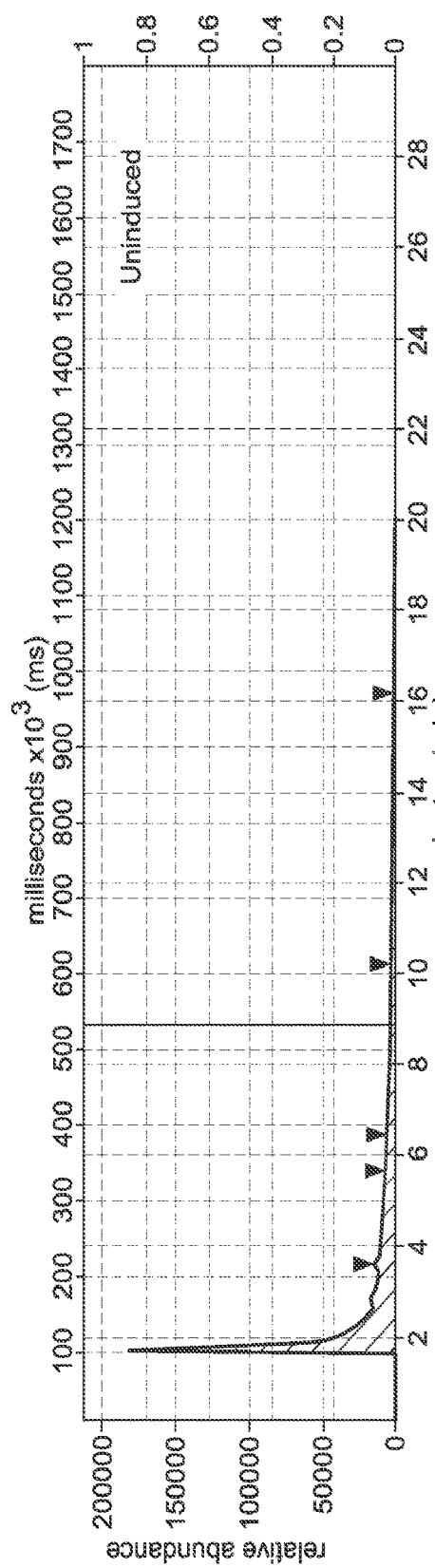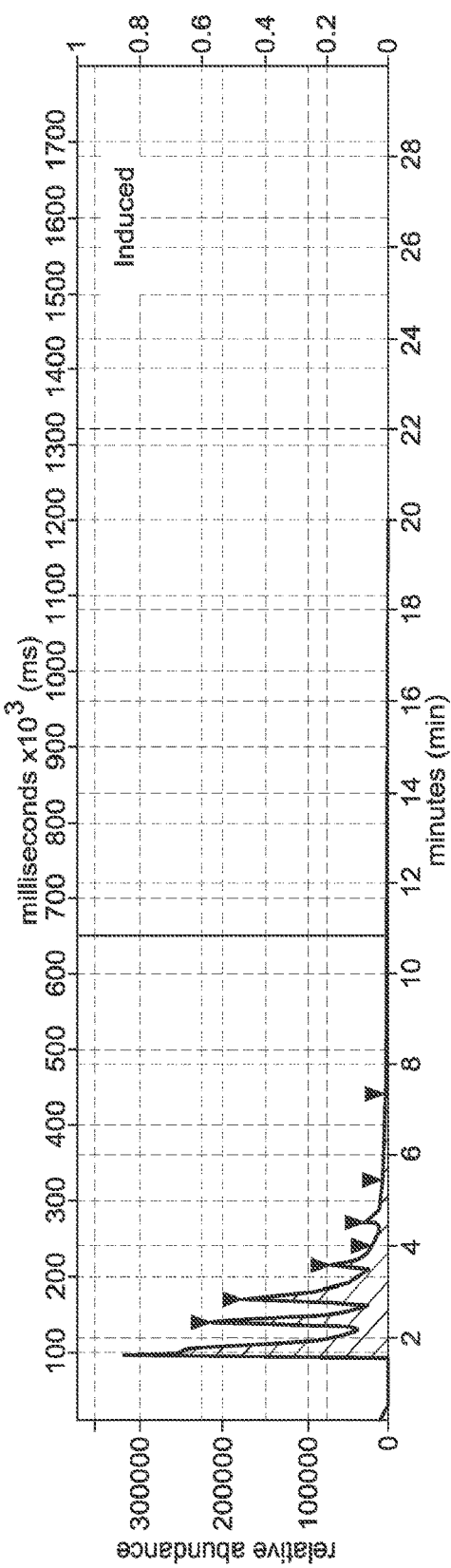
FIG. 3A
FIG. 3B

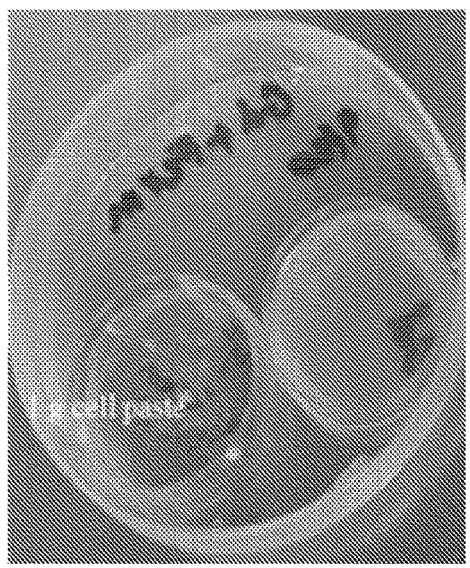 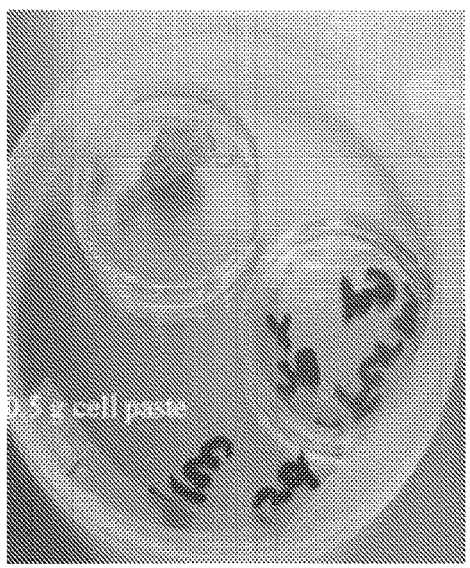
FIG. 6A                FIG. 6B
 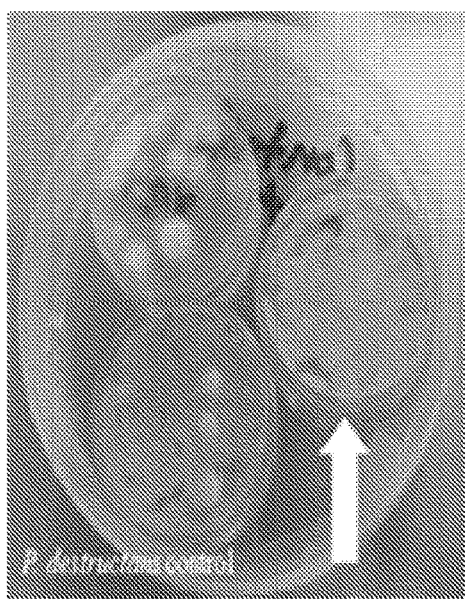
FIG. 6C                FIG. 6D

INHIBITING OR REDUCING FUNGAL INFECTIONS

CROSS-REFERENCE TO RELATED APPLICATIONS

This application claims benefit of U.S. Provisional Application No. 62/010,295, filed Jun. 10, 2014, which is hereby incorporated herein by reference in its entirety.

BACKGROUND

Fungi can be detrimental to many different facets of life. For example, fungi (e.g., mildew or mold) can negatively affect aesthetics or human living conditions, e.g., through degradation/deterioration of material, through contamination, by making material, e.g., wood, appear undesirable, or through production of undesirable toxins.

In the past 10 years, there have increasing reports of fungal (mold) infection epidemics killing off a high percentage of many animals. Such animals devastated by recent mold epidemics include animals as diverse as bats, frogs and bees. For example, bats play a very important role in the ecosystem since they pollinate many cultivated and wild plants and eat large quantities of mosquitoes and other harmful insects. The fungus *Pseudogymnoascus destructans* (formerly *Geomyces destructans*) has been estimated to have killed at least 5.7 to 6.7 million hibernating bats in the eastern US and southeastern Canada. The infection is also known as "white nose syndrome". The *P. destructans* fungus invades the skin, disrupts several physiological functions in the bat and causes death. Some species of bats are now threatened with extinction due to this infection. For example, the little brown bat (*Mytosis lucifugus*) has suffered a 91% hibernating mortality over a single winter.

Honey bees are indispensable to U.S. agriculture, yet their future and the future of the dependent agricultural economies are in peril. The apiculture industry continues to battle the accelerating rate of decline in the health and number of honey bee colonies. One of the causes for this colony collapse is Chalkbrood (*Ascosphaera apis*) and Stonebrood (*Aspergillus fumigatus, Aspergillus flavus*, and *Aspergillus niger*) fungal disease.

Fungi also cause a wide variety of diseases in humans. Some fungi cause infections limited to the outermost layers of the skin and hair (superficial mycoses), other fungi cause cutaneous mycoses by penetrating to the keratinized layers of the skin, hair and nails and triggering pathologic changes in the host. Subcutaneous mycoses cause infections in the dermis, subcutaneous tissues, muscle and fascia and are often chronic. Systemic mycoses typically originate primarily in the lung and from there may cause secondary infections in other organ systems in the body. Patients with immune system deficiencies are often prone to opportunistic mycoses.

There is a need in the art for improved treatment options for human and animals affected by fungal infections. Many of the agents currently used in treating mycotic infections are extremely toxic, causing significant problems/issues with the health and wellbeing of the host. There is a great need for fungal control agents that do not by themselves represent a health hazard to the host taking the anti-fungal. The use of a biologically derived control agent that does not pose a risk to the infected host would represent a significant improvement.

SUMMARY

A method for treating or preventing fungal infection in a subject is provided. The methods comprise exposing the subject to one or more bacteria, one or more enzymes, an enzymatic extract isolated from one or more bacteria, or any combination thereof, in a quantity sufficient to inhibit or reduce fungal growth in the subject. The one or more bacteria can be selected from the group consisting of genus *Rhodococcus*, genus *Brevibacterium*, genus *Pseudonocardia*, genus *Nocardia*, genus *Pseudomonas*, and combinations thereof. The one or more enzymes can be selected from the group consisting of nitrile hydratases, amidases, asparaginases, ACC deaminases, cyanoalanine synthase-like enzymes, monooxygenases, dioxygenases, cyandiases, and combinations thereof.

In certain embodiments, the one or more bacteria are "induced" to exhibit a desired characteristic (e.g., the expression of a desired level of activity of an enzyme of the bacteria) by exposure or treatment with a suitable inducing agent. Inducing agents include, but are not limited to urea, methyl carbamate, cobalt, asparagine, glutamine, and combinations thereof. In some embodiments, the one or more bacteria are exposed to or treated with urea, methyl carbamate, methacrylamide, or acetamide. In some embodiments, the one or more bacteria are exposed to or treated with a mixture of inducing agents comprising urea or methyl carbamate and one or more of asparagine and cobalt. In some embodiments, enzymatic activity in nitrile hydratase producing microorganisms can be induced with amide containing amino acids and derivatives thereof. In some embodiments, enzymatic activity in nitrile hydratase producing microorganisms is stabilized with trehalose.

The details of one or more aspects are set forth in the accompanying drawings and description below. Other features, objects, and advantages will be apparent from the description and drawings and from the claims.

DESCRIPTION OF DRAWINGS

FIG. 3 shows SPME-GC-MS headspace analysis of uninduced (top) and induced (bottom) *Rhodococcus*.

FIG. 6 is a series of images showing non-growth *Rhodococcus* cell paste exhibits strong contact-independent inhibition of growth from conidia of *P. destructans*. Images taken 21 DPI. Experiment conducted at 15° C.

DETAILED DESCRIPTION

Figure 1A:
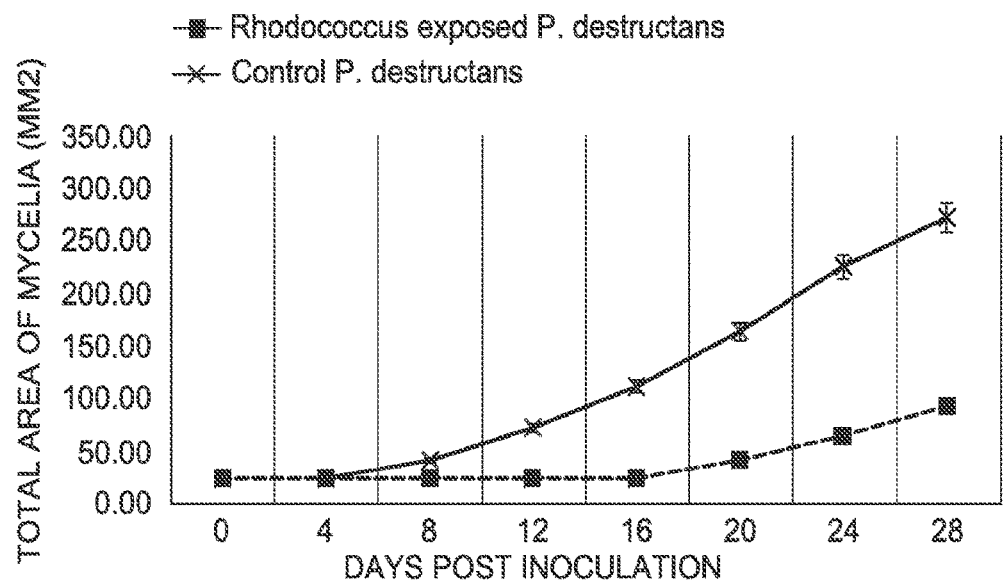
FIGS. 1 and 1B show the effect of *Rhodococcus rhodochrous* DAP 96253 on mycelia area ($mm^2$) for *Pseudogymnoascus destructans* (FIG. 1A) and *Ascosphaera apis* (FIG. 1B) as a function of days after inoculation.

As used herein, the singular forms "a", "an", "the", include plural referents unless the context clearly dictates otherwise.

Throughout the specification the word "comprising," or grammatical variations thereof, will be understood to imply the inclusion of a stated element, integer or step, or group of elements, integers or steps, but not the exclusion of any other element, integer or step, or group of elements, integers or steps.

The disclosed compositions, apparatuses, and methods arise from the surprising finding that one or more bacteria are capable of inhibiting or reducing fungal growth. Therefore, method are disclosed to reduce fungal growth in or on a subject by exposing the subject to a microorganism disclosed herein. This microorganism can be alive and replicating, alive and non-replicating, or dead, so long as the enzymatic activity in the cell is maintained. In other embodiments, the subject is exposed to one or more enzymes produced by the bacteria that are capable of inhibiting or reducing fungal growth. For example, in some embodiments, the enzymes are provided as an enzymatic extract from the disclosed microorganism. When enzymes or enzymatic extracts are used, cofactors can also be present, e.g., endogenous or exogenous cofactors. In some cases, endogenous cofactors are substituted with equivalent cofactors. Regardless of the source, the cofactors can be provided in catalytic amounts and can also be regenerated as needed.

As used throughout, fungal growth includes all stages of the life cycle of a fungus including, but not limited to, spore germination, mycelium growth, and the development and formation of fruiting structures on the fungus.

Provided herein are methods and compositions for treating or preventing one or more fungal infections in a subject. The methods comprise exposing a subject to a composition comprising one or more bacteria, wherein the one or more bacteria are selected from the group consisting of genus *Rhodococcus*, genus *Brevibacterium*, genus *Pseudonocardia*, genus *Nocardia*, genus *Pseudomonas* and combinations thereof, and wherein the one or more bacteria are provided in a quantity sufficient to inhibit or reduce fungal growth in the subject. Optionally, the bacteria are induced to produce one or more enzymes. In some embodiments, the methods comprise exposing the subject to a composition comprising one or more enzymes selected from the group consisting of nitrile hydratases, amidases, asparaginases, ACC deaminases, cyanoalanine synthase-like enzymes, monooxygenases, dioxygenases, cyanidases, and combinations thereof, wherein the enzymes are provided in a quantity sufficient to inhibit or reduce fungal growth in the subject.

The methods and compositions are drawn to inhibiting or reducing fungal growth in a subject. Alternatively or additionally, the methods and compositions inhibit or reduce toxin development or release by a fungus.

The term "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The term "treatment" is not limited to treatment or prescription by a medical professional, but also includes activities conducted by any other individual, including by the subject themselves.

The term "prevent" refers to a treatment administered before onset of a disease or condition that delays the onset of a disease or condition or reduces the severity of the disease or condition. Thus, if a treatment can treat a disease in a subject having symptoms of the disease, it can also prevent that disease in a subject who has yet to suffer some or all of the symptoms.

As defined herein, "inhibiting or reducing fungal growth," and grammatical variants thereof, refers to any slowing, interruption, suppression, delay, or inhibition of the fungal growth. Inhibiting or reducing fungal growth can, for example, comprise inhibiting or reducing growth of resting fungal cells, which can include spore germination, mycelia development, and/or the formation of fruiting structures on the fungus (e.g., sporangia/sporophores).

Fungal growth can, for example, be produced by a fungus selected from the group consisting of mold, yeast, mildew, fungi that cause smut, fungi that cause rust, fungi that cause diseases of plants, and fungi that cause diseases of animals.

The term "subject" refers to any animal that is the target of administration or treatment. The subject can be a vertebrate, for example, a mammal. The term "mammal" is known in the art, and exemplary mammals include humans, primates, livestock animals (including bovines, porcines, etc.), companion animals (e.g., canines, felines, birds, horses, etc.) and rodents (e.g., mice and rats). The subject can be an invertebrate animal, such as an insect or other arthropod. The subject can also be a human or veterinary patient. The term "patient" refers to a subject under the treatment of a clinician, e.g., physician.

In some cases, the subject is a bat. For example, the fungus can comprise *Pseudogymnoascus destructans*. In these aspects, the composition can be applied, for example, to areas in or around a bat roost/hibernacula. The composition can also be provided in a bat lure so the bat takes the catalyst back to its roost/hibernacula. In some cases, the composition is provided as a vegetative probiotic. The composition can also be provided as a non-vegetative agent, e.g., as an ointment or spray. The composition can also be incorporated into a fixed cell matrix and placed on wing tags, arm bands, or collars. The composition can also be incorporated into a nesting structure/anchor upon which bats nest and/or congregates. In some cases, the treatment period is during late swarm or very early hibernation.

In some cases, the subject is a honey bee. For example, the fungus can be selected from the group consisting of *Ascosphaera apis, Nosema apis, Aspergillus fumigatus, Aspergillus flavus*, and *Aspergillus niger*. In these aspects, the composition can be provided in a bait particle. For example, the bait particle can be a microparticle configured to simulate a pollen particle such that a bee will pick up the particle and return it to the hive. In some embodiments, the bat particle is adhesive. The composition can also be provided in a wax, such as a beeswax. In these embodiments, the wax can be incorporated directly into a bee hive. The composition can also be provided as a powder, and optionally mixed with powdered sugar for application as a dust to the hive. The composition can also be incorporated into wax (bee wax, paraffin, etc.) and used as a base layer for hive frames. Hive frames are generally wooden structure that bees build combs on. Wax foundations are often included as a starting point for the bees, which could be supplemented with the disclosed composition. In some cases, the composition is added beneath the hive (open center concept), e.g., as a tray of cells. Without wishing to be bound by theory, this can result in VOCs that permeate the hive and are drawn into the hive by convection (hives are warmer inside compared to ambient temp.) The composition can also be provided as a probiotic in supplemental feed. For example, sugar solutions are typically provided by keepers in winter to supplement their diet, which can be supplemented with the disclosed composition. The composition can also be incorporated into a material at the entrance to the hive “door mat” whereby the bees come in contact with the material and bring it into the hive. This type of application takes advantage of the grooming habits of the bees to distribute the material throughout the colony.

In some cases, the subject is a snake or lizard. For example, the fungus can be Snake Fungal Disease or Yellow Fungus Syndrome. In these embodiments, the composition can, for example, be applied directly to the animal (probiotic), sprayed into burrows (environmental control), or delivered as a bait. Fungal infections in snakes are typically in their facial area, so a bait could be an effective delivery system for delivery of the disclosed compositions to affected areas.

In some cases, the subject is a human or veterinary patient. For cats and dogs, for example, delivery may be accomplished by an ointment, liquid, aerosol or spray. In the composition is administered in a manner that prevents the animal from licking off the agent or bother the site being treated. For example, the composition can be administered in a manner that quickly dries. In some embodiments, cleaning agents are used to “prep” and clean the affected area permitting better contact and dosing with the disclosed compositions. In some cases, a mild anesthetic is used to reduce irritation. This anesthetic can be administered separately or in the same composition with the disclosed bacteria, enzymes, or enzymatic extracts.

Fungi cause a wide variety of diseases in humans. While some fungi cause infections limited to the outermost layers of the skin and hair (superficial mycoses), other fungi cause cutaneous mycoses by penetrating to the keratinized layers of the skin, hair and nails and triggering pathologic changes in the host. Subcutaneous mycoses cause infections in the dermis, subcutaneous tissues, muscle and fascia and are often chronic. Systemic mycoses originate primarily in the lung and may cause secondary infections in other organ systems in the body. Patients with immune system deficiencies are often prone to opportunistic mycoses.

Examples of *Microsporum* species include *M. canis* and *M. gypseum. Microsporum* is one of the several fungal genera that cause dermatophytosis. Dermatophytosis is a general term used to define the infection in hair, skin or nails due to any dermatophyte species. Similar to other dermatophytes, *Microsporum* has the ability to degrade keratin and thus can reside on skin and its appendages and remains noninvasive. Notably, *Microsporum* spp. mostly infect the hair and skin. *Microsporum canis* is the principal cause of ringworm in dogs and cats and a zoophilic fungal species causing sporadic dermatophytosis in humans, especially tinea capitis in children with cats and dogs.

Skin infection by a *Trichophyton* species occurs mainly on the back of the neck, scalp or beard. Symptoms of a *Trichophyton* species infection include inflamed scalp lesions, inflamed neck lesions, inflamed beard lesions, scarring, and permanent hair loss. Examples of *Trichophyton* species include *T. rubrum, T. tonsurans* and *T. mentagrophytes.*

*Trichophyton tonsurans* is an anthropophilic endothrix species of fungi that causes epidemic dermatophytosis in Europe, South America, and the U.S. It infects some animals and requires thiamine for growth. It is the most common cause of tinea capitis in the U.S., forming black dots where hair breaks off at the skin surface. *Trichophyton rubrum* is a fungus that is the most common cause of tinea pedis (athlete’s foot), tinea cruris, and tinea (ringworm). *Trichophyton rubum* is the most common of the dermatophytes causing fingernail fungus infections. While most fungal skin infections are irritating and difficult to treat, there are reports of fungal infections resulting in death, such as *Trichophyton mentagrophytes* skin infection migrated to the lymph nodes, testes, vertebrae and CNS.

The genus *Epidermophyton* contains two species; *Epidermophyton floccosum* and *Epidermophyton stockdaleae. E. stockdaleae* is known to be nonpathogenic, leaving *E. floccosum* as the only species causing infections in humans. *E. floccosum* is one of the common causes of dermatophytosis in otherwise healthy individuals. It infects skin (tinea corporis, tinea cruris, tinea pedis) and nails (onychomycosis). The infection is restricted to the nonliving cornified layers of epidermis since the fungus lacks the ability to penetrate the viable tissues of the immunocompetent host. Disseminated infections due to any of the dermatophytes are very unlikely due to the restriction of the infection to keratinized tissues. However, invasive *E. floccosum* infection has been reported in an immunocompromised patient with Behcet’s syndrome. As with all forms of dermatophytosis, *Epidermophyton floccosum* infections are communicable and usually transmitted by contact, particularly in common showers and gym facilities.

Examples of *Candida* species include *C. albicans, C. parapsiliosis*, and *C. krusei*. Patients with chronic mucocutaneous candidiasis may develop *candida* infection of the nails. *Candida* species may invade nails previously damaged by infection or trauma and cause infection in the periungual area and underneath the nailbed. The nailfold becomes erythematous, swollen and tender with an occasional discharge. The disease causes loss of the cuticle, nail dystrophy, and onycholysis with discoloration around the lateral nailfold. In all forms of onychomycosis, the nail becomes variously disfigured and distorted. A specific example of a fungal infection caused by the fungi and yeasts discussed above is onychomycosis (nail infection). Fungal infections affecting the nails or scalp are very difficult to treat due to fungal infection in follicle roots or under the nail itself.

Onychomycosis is a chronic, persistent fungal, yeast, and/or mold infection of the nail bed which causes thickening and discoloration of the nail, sometimes accompanied by pain and disability. This fungal infection affects 25% of adults, and the incidence rises with age, such that the prevalence in adults over 50 years of age is 40%. According to a study reported in Podiatry Today, over 35 million people in the United States have onychomycosis, and up to 50% of those affected by the disease do not receive treatment.

In addition, *Candida* species, and *Candida albicans* in particular, play an etiologic role in the development of chronic paronychia, a common infection of the soft tissue around the fingernail or toenail, where bacteria may act as co-pathogens. Swollen, erythematous and tender nail folds without fluctuance are characteristic of chronic paronychia. Eventually, the nail plates become thickened and discolored, with pronounced transverse ridges and the cuticles and nail folds may separate from the nail plate, forming a space for the invasion of various microorganisms. Onychomycosis has long been one of the most difficult fungal infections to treat. The length of time it takes the nail to grow, the impenetrability of the nail plate, and location of the infection between the nail bed and plate are major factors interfering with the eradication of fungal agents affecting these tissues. Thus, eradication of symptoms is very slow and may take a whole year or even longer. Topical antifungals have low efficacy because of their antifungal spectrum may be limited to dermatophytes and because of restricted penetration of the antifungal agent across the nail. Systemic treatment with antifungal agents has shown relapse rates of 40% or higher, and have significant risks, including hepatic and/or cardiac toxicity, and adverse drug interactions. Thus, there is a significant need for alternative, and more effective, methods of treating fungal, yeast, and/or mold infections such as onychomycosis.

Therefore, in some embodiments, the disclosed compositions are directly applied to the skin or nails of a subject, e.g., in the form of an ointment. In particular cases, this can be used to treat or prevent, for example, *Geomyces pannorum*.

The disclosed compositions can also be used in containers used to store items that need to be kept sterile for human use. For example, the disclosed compositions can be incorporated into contact lens storage containers, e.g., as a fixed cell application. In particular cases, this can be used to treat or prevent, for example, *Fusarium oxysporum* or *Fusarium solani*.

Systemic mycoses due to opportunistic pathogens are infections of patients with immune deficiencies who would otherwise not be infected. Examples of immunocompromised conditions include AIDS, alteration of normal flora by antibiotics, immunosuppressive therapy, and metastatic cancer. Examples of opportunistic mycoses include *Candidiasis, Cryptococcosis* and *Aspergillosis*.

In some embodiments, the disclosed compositions are used for environmental control in a home or health facility where opportunistic mycoses can occur. For example, the disclosed compositions can be imbedded in an air-filter. In particular cases, this can be used to treat or prevent, for example, *Aspergillus fumigatus* or *Aspergillus flavus*.

In some embodiments, the disclosed compositions are used for to treat or prevent infection of wounds and burns, which are susceptible to infection by microorganisms, such as bacteria and fungi. Microbial infection typically slows or prevents the healing of a wound or burn, and may lead to a localized or systemic infection of the wounded or burned organism. Accordingly, in some aspects a method is provided for inhibiting the growth of microorganisms in, or on, living tissue. These methods can include the step of contacting living tissue that is infected with microorganisms with a composition disclosed herein in amounts sufficient to inhibit growth of the microorganisms. In some embodiments, the living tissue has been wounded or burned.

As used herein, the term "wound" encompasses physical injuries to living tissue and/or interruption to the integrity of living tissue, such as cuts, tears, abrasions, and lesions and crushed tissue, as well as pimples, ulcers and hemorrhoids.

The term "wound dressing" refers to a material that is used to cover a wound. Examples of wound dressings include ointments, gels, salves, bandages and gauze.

A variety of living tissues of an animal body can be treated using the disclosed composition and methods. For example, the methods can be used to inhibit the growth of microorganisms on skin lesions, burns on the skin, or on wounds (such as cuts or abrasions) of the skin. The methods can also be used, for example, to inhibit the growth of microorganisms within a body cavity (e.g., abdomen) or a joint (e.g., a knee joint), on the surface of an eye, or in the mouth.

In some embodiments, the disclosed bacteria, enzyme, and/or the enzymatic extract isolated from the bacteria are applied to a wound dressing that is administered to the wound or site of infection. In some embodiments, the disclosed bacteria, enzyme, and/or the enzymatic extract isolated from the bacteria are introduced onto the surface of an eye, or into the ear canal, using a dropper. Ointments, creams or gels comprising bacteria, enzyme, and/or the enzymatic extract isolated from the bacteria, may, for example, be rubbed onto a surface of a living organism. Other examples of methods for contacting living tissue with a composition comprising bacteria, enzyme, and/or the enzymatic extract isolated from the bacteria include flushing or irrigating the living tissue with a solution containing bacteria, enzyme, and/or the enzymatic extract isolated from the bacteria; rubbing living tissue with a medical dressing containing a solution containing bacteria, enzyme, and/or the enzymatic extract isolated from the bacteria; spraying living tissue (e.g., by using a nebulizer) with a composition containing bacteria, enzyme, and/or the enzymatic extract isolated from the bacteria; introducing a solution containing bacteria, enzyme, and/or the enzymatic extract isolated from the bacteria into a living body using, for example, a tube, catheter, canula or endoscopic device; introducing a composition containing bacteria, enzyme, and/or the enzymatic extract isolated from the bacteria into an orifice of a living body using, for example, a suppository or tampon; and contacting oral tissue with a composition containing bacteria, enzyme, and/or the enzymatic extract isolated from the bacteria, for example by gargling or rinsing the oral cavity with a composition containing bacteria, enzyme, and/or the enzymatic extract isolated from the bacteria.

Wound dressings suitable for use in the disclosed methods can be any material that is biologically acceptable and suitable for placing on a wound. In exemplary embodiments, the wound dressing may be a woven or non-woven fabric of synthetic or nonsynthetic fibers, or any combination thereof. For example, the wound dressing can be gauze. The gauze may be absorbent and can be, for example, wetted with a composition containing bacteria, enzyme, and/or the enzymatic extract isolated from the bacteria. The dressing may also comprise a support, such as a polymer foam, a natural or man-made sponge, a gel or a membrane that may absorb or have disposed thereon, a composition containing bacteria, enzyme, and/or the enzymatic extract isolated from the bacteria. Again by way of example, the support can be a film, a natural or synthetic polymer, or a rigid or malleable material.

In some embodiments, the disclosed compositions and methods can also treat or prevent bacterial infections in a subject, e.g., in wounds or burns. Without wishing to be bound by theory, this effect of the disclosed compositions may be due to quorum quenching mechanism. In particular cases, this can be used to treat or prevent, for example, *Pseudomonas aeruginosa* or *Burkholderia cepacia*.

The disclosed compositions and methods can also be used to treat or prevent infections in domestic animals such as dogs, cats, and birds. In particular cases, this can be used to treat or prevent, for example, *Microsporum canis* (dogs, cats), *Aspergillus flavus, A. fumigatus* (dogs, birds), and *Trichophyton verrucosum*.

The disclosed compositions and methods can also be used to prevent toxicosis from aflatoxin exposure. Aflatoxin-producing members of *Aspergillus* are common and widespread in nature. They can colonize and contaminate grain before harvest or during storage. Host crops, which include maize, sorghum, and groundnuts, are particularly susceptible to infection by *Aspergillus* following prolonged exposure to a high-humidity environment, or damage from stressful conditions such as drought, a condition that lowers the barrier to entry. The toxin also may be found in the milk of animals that are fed contaminated feed. High-level aflatoxin exposure produces an acute hepatic necrosis, resulting later in cirrhosis, or carcinoma of the liver. Acute liver failure is made manifest by bleeding, edema, alteration in digestion, changes to the absorption and/or metabolism of nutrients, and mental changes and/or coma.

In certain embodiments, the methods and compositions for inhibiting or reducing fungal growth comprises exposing the subject to one or more bacteria selected from the group consisting of genus *Rhodococcus*, genus *Brevibacterium*, genus *Pseudomonas*, genus *Nocardia*, genus *Pseudonocardia* and combinations thereof. The one or more bacteria can, for example, include *Rhodococcus* spp. The *Rhodococcus* spp can, for example, include *Rhodococcus rhodochrous* DAP 96253 strain, *Rhodococcus rhodochrous* DAP 96622 strain, *Rhodococcus erythropolis*, or combinations thereof. Optionally, the compositions comprise *Rhodococcus rhodochrous* and *Rhodococcus erythropolis*. Exemplary organisms include, but are not limited to, *Pseudomonas chloroaphis* (ATCC 43051) (Gram-negative), *Pseudomonas chloroaphis* (ATCC 13985) (Gram-negative), *Rhodococcus erythropolis* (ATCC 47072) (Gram-positive), and *Brevibacterium ketoglutamicum* (ATCC 21533) (Gram-positive). Examples of *Nocardia* and *Pseudonocardia* species have been described in European Patent No. 0790310; Collins and Knowles J. Gen. Microbiol. 129:711-718 (1983); Harper Biochem. J. 165:309-319 (1977); Harper Int. J. Biochem. 17:677-683 (1985); Linton and Knowles J Gen. Microbiol. 132:1493-1501 (1986); and Yamaki et al., J. Ferm. Bioeng. 83:474-477 (1997).

Although in some embodiments the one or more bacteria are selected from the group consisting of *Rhodococcus* spp., *Brevibacterium ketoglutamicum*, and *Pseudomonas chloroaphis*, any bacterium that inhibits or reduces fungal growth when exposed to an animal can be used in the present methods. For example, bacteria belonging to the genus *Nocardia* [see Japanese Patent Application No. 54-129190], *Rhodococcus* [see Japanese Patent Application No. 2-470], *Rhizobium* [see Japanese Patent Application No. 5-236977], *Klebsiella* [Japanese Patent Application No. 5-30982], *Aeromonas* [Japanese Patent Application No. 5-30983], *Agrobacterium* [Japanese Patent Application No. 8-154691], *Bacillus* [Japanese Patent Application No. 8-187092], *Pseudonocardia* [Japanese Patent Application No. 8-56684], *Burkholderia, Corynebacterium*, and *Pseudomonas* are non-limiting examples of bacteria that can be used. Not all species within a given genus exhibit the same type of enzyme activity and/or production. Thus, it is possible to have a genus generally known to include strains capable of exhibiting a desired activity but have one or more strains that do not naturally exhibit the desired activity or one or more strains which do not exhibit the activity when grown on the same medium as the species which exhibit this activity. Thus, host microorganisms can include strains of bacteria that are not specifically known to have the desired activity but are from a genus known to have specific strains capable of producing the desired activity. Such strains can have transferred thereto one or more genes useful to cause the desired activity. Non-limiting examples of such strains include *Rhodococcus equi* and *Rhodococcus globerulus* PWD1.

Further, specific examples of bacteria include, but are not limited to, *Nocardia* sp., *Rhodococcus* sp., *Rhodococcus rhodochrous, Klebsiella* sp., *Aeromonas* sp., *Citrobacter freundii, Agrobacterium rhizogenes, Agrobacterium tumefaciens, Xanthobacter flavus, Erwinia nigrifluens, Enterobacter* sp., *Streptomyces* sp., *Rhizobium* sp., *Rhizobium loti, Rhizobium legminosarum, Rhizobium merioti, Pantoea agglomerans, Klebsiella pneumoniae* subsp. *pneumoniae, Agrobacterium radiobacter, Bacillus smithii, Pseudonocardia thermophila, Pseudomonas chloroaphis, Rhodococcus erythropolis, Brevibacterium ketoglutamicum*, and *Pseudonocardia thermophila*. Optionally, the microorganisms used can, for example, comprise *Rhodococcus rhodochrous* DAP 96253 and *Rhodococcus rhodochrous* DAP 96622, and combinations thereof.

As used herein, exposing a subject to one or more bacteria includes, for example, exposing the subject to intact bacterial cells, bacterial cell lysates, and/or bacterial extracts that possess enzymatic activity (i.e., "enzymatic extracts"). Methods for preparing lysates and enzymatic extracts from cells, including bacterial cells, are routine in the art. Optionally, the one or more bacteria or enzymatic extracts are fixed with glutaraldehyde and crosslinked. Optionally, the crosslinked, glutaraldehyde-fixed bacteria or extract is formulated with a carrier into a spray.

In certain embodiments, the methods and compositions for inhibiting or reducing fungal growth comprise exposing the subject to an enzyme. The enzyme can be selected from the group consisting of nitrile hydratase, amidase, asparaginase, ACC (1-aminocyclopropane-1-carboxylic acid) deaminase, cyanoalanine synthase-like enzyme, alkane monooxygenase, ammonium monooxygenase, methane monooxygenase, toluene dioxygenase, cyanidase, and/or a combination thereof. The enzyme can be provided within a composition for exposure to the subject. The enzyme can also be a purified enzyme or can be provided as an enzymatic extract as described above. Optionally, the methods for inhibiting or reducing fungal growth in a animal comprise exposing the location to a composition comprising an enzyme, the enzyme being selected from one or more of nitrile hydratase, amidase, asparaginase, ACC deaminase, cyanoalanine synthase-like enzyme, alkane monooxygenase, ammonium monooxygenase, methane monooxygenase, toluene dioxygenase, and cyanidase. The one or more bacteria, enzymatic extract, or enzymes used in the methods may at times be more generally referred to herein as the "catalyst."

In the methods provided herein, the subject or its habitat is exposed to one or more bacteria, one or more enzymes, enzymatic extract isolated from or derived from the one or more bacteria, or any combination thereof, in a quantity sufficient to inhibit or reduce fungal growth. In some embodiments, the subject or its habitat is exposed to one or more bacteria in combination with one or more exogenous enzymes and/or enzymatic extracts. "Exogenous" refers to enzymes or enzymatic extracts that are isolated and/or purified ex situ and is distinguished from enzymes produced by bacteria in situ. This combined exposure can take place simultaneously and/or sequentially. For example, the subject or its habitat can be exposed to exogenous enzymes and/or enzymatic extracts 1 to 60 minutes, 1 to 24 hours, or 1 to 7 days after exposure to the bacteria.

"Exposing" a subject or its habitat to one or more bacteria, one or more enzymes, and/or an enzymatic extract includes any method of presenting a bacterium, enzyme, and/or extract to the subject or its habitat. Optionally, the subject or its habitat is indirectly exposed to the one or more bacteria, one or more enzymes, and/or the enzymatic extract. Indirect methods of exposure include, for example, placing the one or more bacteria, one or more enzymes, and/or enzymatic extract in the general proximity of the subject or its habitat (i.e., indirect exposure). Optionally, the subject or its habitat is directly exposed to one or more bacteria, one or more enzymes, and/or the enzymatic extract, whereby the one or more bacteria, one or more enzymes, and/or enzymatic extract are in direct contact with the subject or its habitat.

Without wishing to be bound by theory, in some embodiments, indirect exposure results in volatile organic compound (VOC) release from the bacteria that contacts the subject and inhibits or reduces fungal growth.

In certain embodiments, exposure of the bacteria, enzyme, and/or the enzymatic extract isolated from the bacteria can occur, for example, by providing the bacteria, enzyme, and/or enzymatic extract in liquid form and spraying it onto or near the subject or its habitat. The bacteria, enzyme, and/or enzymatic extract can, for example, further comprise a liquid carrier. Liquid carriers can be selected from the group consisting of an aromatic hydrocarbon, a substituted naphthalene, a phthalic acid ester, an aliphatic hydrocarbon, an alcohol, and a glycol. Optionally, the liquid carrier can be a wax or similar type material coating, which could be applied to the plant as a liquid, but would be solid at ambient or lower temperatures. Optionally, the bacteria, enzyme and/or enzymatic extract are provided onto or near the subject or its habitat by a fog or spray. For example, the bacteria, enzyme or enzymatic extract can be provided to a habitat where the fungi is to be controlled.

In certain embodiments, exposure of the one or more bacteria, one or more enzymes, and/or the enzymatic extract isolated from the bacteria can occur, for example, by providing the bacteria, enzyme, and/or enzymatic extract in solid form and dusting it onto or near the subject or its habitat. The bacteria, enzyme, and/or enzymatic extract can, for example, further comprise a solid carrier. The solid carrier can be selected from the group consisting of a dust, a wettable powder, a water dispersible granule, and mineral fillers. Optionally, the solid carrier is a mineral filler. Mineral fillers can, for example, be selected from the group consisting of a calcite, a silica, a talc, a kaolin, a montmorillonite, and an attapulgite. Other solid supports for use with the bacteria, enzyme, and/or enzymatic extract are described herein.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

In certain embodiments, the one or more bacteria, one or more enzymes, and/or enzymatic extract further comprise a coating, wherein the coating makes the one or more bacteria, one or more enzymes, and/or enzymatic extract water resistant. The coating can be selected from a hydrophobic fatty acid polyester coating or a wax. Optionally, the hydrophobic fatty acid polyester coating is a long chain fatty acid polyester derived from sucrose, sorbitol, sorbinose, glycerol, or raffinose.

Also provided herein are compositions for inhibiting or reducing fungal growth. The compositions can, for example, comprise one or more bacteria, one or more enzymes, and/or one or more enzymatic extracts capable of inhibiting or reducing fungal growth. The compositions can further comprise solid, liquid, aerosols, gels, and gelatinous carriers, as disclosed above, and/or media and media components for inducing and stabilizing the one or more bacteria, one or more enzymes, and/or enzymatic extracts, as disclosed below. Optionally, the compositions can be converted into pellet form for distribution or application to the subject or its habitat.

Optionally, the one or more bacteria, one or more enzymes, and/or enzymatic extract are used in combination with other agents that inhibit or reduce fungal growth. For example, the provided methods can further comprise the step of exposing the subject or its habitat to an agent that inhibits or reduces fungal growth, e.g., a fungicide. Likewise, the provided compositions can further comprise an agent that inhibits or reduces fungal growth, e.g., a fungicide. Agents that inhibit or reduce fungal growth include, but are not limited to, anthocyanins, organic acids, such as, propionic acid and sorbic acid, aluminosilicates, clays, zeolites, and calcium propanoate.

The provided composition(s) can also be used in combination with one or more classes of antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, Vancomycin).

As defined herein, a "sufficient" quantity or effective amount of the bacteria, enzyme, and/or enzymatic extract will depend on a variety of factors, including, but not limited to, the particular bacteria, enzyme, and/or enzymatic extract utilized in the method, the form in which the bacteria is exposed to the location (e.g., as intact bacterial cells (dead or alive), cell lysates, enzymatic extracts, and/or enzymes as described above), the means by which the bacteria, enzyme, and/or enzymatic extract is exposed to the location, the length of time of the exposure, and the type and amount of fungal signal compounds that result in the inhibition or reduction of fungal growth. Optionally, the quantity of bacteria exposed to the location is in the range of 1 to 250 mg of cell-dry weight or the equivalent thereof for enzymatic extracts and enzymes. For example, for 1 mg of dry weight of cells, typically there are 150-300 units of nitrile hydratase, 10-25 units of amidase, 7-15 units of cyanidase, 7-20 units of ACC deaminase, and 7-20 units of cyanoalanine synthase-like enzyme. By way of other examples, the quantity of bacteria exposed to the location is in the range of 0.1 mg to 1 g, 0.1 to 400 mg, 1 to 200 mg, 1 to 80 mg, or 1 to 10 mg of cell-dry weight or the equivalent thereof for enzymatic extracts and enzymes. By way of example, the quantity of bacteria exposed to the subject or its habitat is, for example, in the range of 0.1 mg to 1 g per 9-10 kilos (kg) of plant or plant part. It would be a matter of routine experimentation for the skilled artisan to determine the "sufficient" quantity of the one or more bacteria, one or more enzymes, or enzymatic extract necessary to inhibit or reduce fungal growth. For example, if the bacteria, one or more enzymes, or enzymatic extract necessary to inhibit or reduce fungal growth are immobilized or stabilized, the quantity of bacteria, one or more enzymes, or enzymatic extract is adjusted to inhibit or reduce fungal growth.

In certain embodiments, the one or more bacteria are "induced" to exhibit a desired characteristic (e.g., the expression of a desired level of activity of an enzyme of the bacteria) by exposure or treatment with a suitable inducing agent. Inducing agents include, but are not limited to urea, methyl carbamate, cobalt, asparagine, glutamine, and combinations thereof. Optionally, the one or more bacteria are exposed to or treated with urea, methyl carbamate, methacrylamide, or acetamide. Optionally, the one or more bacteria are exposed to or treated with a mixture of inducing agents comprising urea or methyl carbamate and one or more of asparagine and cobalt. In some embodiments, the compositions and methods optionally exclude an inducing agent, such as cobalt.

The inducing agent, when used, can be added at any time during cultivation of the desired cells. For example, with respect to bacteria, the culture medium can be supplemented with an inducing agent prior to beginning cultivation of the bacteria. Alternately, the bacteria could be cultivated on a medium for a predetermined amount of time to grow the bacteria and the inducing agent could be added at one or more predetermined times to induce the desired enzymatic activity in the bacteria. Moreover, the inducing agent could be added to the growth medium (or to a separate mixture including the previously grown bacteria) to induce the desired activity in the bacteria after the growth of the bacteria is completed or during a second growth or maintenance phase.

While not intending to be limited to a particular mechanism, "inducing" the bacteria may result in the production or activation (or increased production or increased activity) of one or more of enzymes, such as nitrile hydratase, amidase, asparaginase, ACC deaminase, cyanoalanine synthase-like enzyme, alkane monooxygenase, ammonium monooxygenase, methane monooxygenase, toluene dioxygenase, and/or cyanidase, and the induction of one or more of these enzymes may play a role in inhibiting or reducing fungal growth. "Nitrile hydratases," "amidases," "asparaginases," "ACC deaminases," "cyanoalanine synthase-like enzymes," "AMO-type (alkane or ammonium) monooxygenases," "methane monooxygenases," "toluene dioxygenases," and "cyanidases" comprise families of enzymes present in cells from various organisms, including but not limited to, bacteria, fungi, plants, and animals. Such enzymes are well known, and each class of enzyme possesses recognized enzymatic activities.

The methods of inducing an enzymatic activity can be accomplished without the requirement of introducing hazardous nitriles, such as acrylonitrile, into the environment. Previously, it was believed that induction of specific enzyme activity in certain microorganisms required the addition of chemical inducers. For example, in the induction of nitrile hydratase activity in *Rhodococcus rhodochrous* and *Pseudomonas chloroaphis*, it was generally believed to be necessary to supplement with hazardous chemicals, such as acetonitrile, acrylonitrile, acrylamide, and the like. However, enzymatic activity in nitrile hydratase producing microorganisms can be induced with the use of non-hazardous media additives, such as amide containing amino acids and derivates thereof, and optionally stabilized with trehalose. Optionally, asparagine, glutamine, or combinations thereof, can be used as inducers. Methods of inducing and stabilizing enzymatic activity in microorganisms are described in U.S. Pat. Nos. 7,531,343 and 7,531,344, which are incorporated herein by reference.

The disclosed methods of inducing enzymatic activity provide for the production and stability of a number of enzymes using modified media, immobilization, and stabilization techniques, as described herein. For example, enzymatic activity can be induced and stabilized through the use of media comprising amide-containing amino acids, or derivatives thereof, and, optionally stabilized by, trehalose. In some embodiments, the methods of induction and stabilization comprise culturing a nitrile hydratase producing microorganism in a medium comprising one or more amide containing amino acids or derivatives thereof, and, optionally, trehalose. Optionally, disclosed are methods for inducing nitrile-hydratase using a medium supplemented with amide containing amino acids or derivatives thereof, which preferably include asparagine, glutamine or a combination thereof. Optionally, disclosed are methods for inducing nitrile-hydratase using a nutritionally complete medium supplemented with only asparagine. Optionally, disclosed are methods for inducing nitrile-hydratase using a nutritionally complete medium supplemented with only glutamine. Optionally, disclosed are methods for stabilizing nitrile-hydratase using a nutritionally complete medium supplemented with only trehalose. More particularly, the methods of induction and stabilization comprise culturing the microorganism in the medium and optionally collecting the cultured microorganisms or enzymes produced by the microorganisms.

Induction and stabilization of enzymes can be achieved without the use of hazardous nitriles. However, while the induction methods eliminate the need for hazardous chemicals for enzyme activity induction, the use of such further inducers is not excluded. For example, one or more nitriles could be used to assist in specific activity development. Media supplemented with succinonitrile and cobalt can be useful for induction of enzymes, including, for example, nitrile hydratase, amidase, asparaginase I, ACC deaminase, cyanoalanine synthase-like enzyme, alkane monooxygenase, ammonium monooxygenase, methane monooxygenase, toluene dioxygenase, and cyanidase. However, the use of nitriles is not necessary for induction of enzyme activity. While the use of nitriles and other hazardous chemicals is certainly not preferred, optionally, such use is possible.

Stabilization of enzyme activity can be achieved through immobilization methods, such as affixation, entrapment, and cross-linking, thereby, extending the time during which enzyme activity can be used. Thus, in some embodiments, induction methods and methods of delaying a chill injury response further comprise at least partially immobilizing the microorganism. Stabilization can be provided by immobilizing the enzymes, enzymatic extracts, or microorganisms producing the enzymes or enzymatic extracts. For example, enzymes or enzymatic extracts harvested from the microorganisms or the induced microorganisms themselves can be immobilized to a substrate as a means to stabilize the induced activity. Optionally, the nitrile hydratase producing microorganisms are at least partially immobilized. Optionally, the enzymes or microorganisms are at least partially entrapped in or located on the surface of a substrate. This allows for presentation of an immobilized material with induced activity (e.g., a catalyst) in such a manner as to facilitate reaction of the catalyst with an intended material and recovery of a desired product while simultaneously retaining the catalyst in the reaction medium and in a reactive mode. In certain embodiments, the stabilization through immobilization methods, such as affixation and entrapment, of the one or more bacteria kills or inactivates the one or more bacteria. Thus, optionally, the induced microorganisms used in the present methods are dead (killed) or inactivated, but are still capable of exhibiting catalyst activity.

Any substrate generally useful for affixation of enzymes, enzymatic extracts, or microorganisms can be used. Optionally, the substrate comprises alginate or salts thereof. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. Optionally, calcium alginate is used as the substrate. The calcium alginate can, for example, be cross-linked, such as with polyethyleneimine, to form a hardened calcium alginate substrate. Further description of such immobilization techniques can be found in Bucke, "Cell Immobilization in Calcium Alginate," Methods in Enzymology, vol. 135, Part B (ed. K. Mosbach) pp. 175-189 (1987), which is incorporated herein by reference. The stabilization effect of immobilization using polyethylenimine cross-linked calcium alginate is discussed in U.S. Pat. No. 7,943,549, which is hereby incorporated by reference in its entirety.

Optionally, the substrate comprises an amide-containing polymer. Any polymer comprising one or more amide groups can be used. Optionally, the substrate comprises a polyacrylamide polymer.

Stabilization can further be achieved through cross-linking. For example induced microorganisms can be chemically cross-linked to form agglutinations of cells. Optionally, the induced microorganisms are fixed and cross-linked using glutaraldehyde. For example, microorganisms can be suspended in a mixture of de-ionized water and glutaraldehyde followed by addition of polyethylenimine until maximum flocculation is achieved. The cross-linked microorganisms (typically in the form of particles formed of a number of cells) can be harvested by simple filtration. Further description of such techniques is provided in Lopez-Gallego, et al., J. Biotechnol. 119:70-75 (2005), which is incorporated herein by reference. In certain embodiments, the cross-linking kills or inactivates the microorganism. Thus, optionally, the induced microorganisms used in the present methods are dead (killed) or inactivated, but are still capable of exhibiting catalyst activity.

Optionally, the microorganisms, enzymes, and/or enzymatic extracts can be encapsulated rather than allowed to remain in the classic Brownian motion. Such encapsulation facilitates collection, retention, and reuse of the microorganisms and generally comprises affixation of the microorganisms to a substrate. Such affixation can also facilitate stabilization of the microorganisms, enzymes, and/or enzymatic extracts as described above, or may be solely to facilitate ease of handling of the induced microorganisms, enzymes, or enzymatic extracts.

The microorganisms, enzymes, and/or enzymatic extracts can be immobilized by any method generally recognized for immobilization of microorganisms, enzymes, and/or enzymatic extracts such as sorption, electrostatic bonding, covalent bonding, and the like. Generally, the microorganisms, enzymes, and/or enzymatic extracts are immobilized or entrapped on a solid support which aids in the recovery of the microorganisms enzymes, or enzymatic extracts from a mixture or solution, such as a detoxification reaction mixture. Suitable solid supports include, but are not limited to, granular activated carbon, compost, wood or wood products, (e.g., paper, wood chips, wood nuggets, shredded pallets or trees), bran (e.g., wheat bran), metal or metal oxide particles (e.g., alumina, ruthenium, iron oxide), ion exchange resins, DEAE cellulose, DEAE-SEPHADEX® polymer, waxes/coating materials (such as those used as a coating for fruits and vegetables and inanimate surfaces), ceramic beads, cross-linked polyacrylamide beads, cubes, pills, or other gel forms, alginate beads, K-carrageenan cubes, as well as solid particles that can be recovered from the aqueous solutions due to inherent magnetic ability. The shape of the catalyst is variable (in that the desired dynamic properties of the particular entity are integrated with volume/surface area relationships that influence catalyst activity). Optionally, the induced microorganism is immobilized in alginate beads that have been cross-linked with polyethyleneimine or is immobilized in a polyacrylamide-type polymer.

In some embodiments, the compositions and medium used in the induction and stabilization methods further comprise one or more amide containing amino acids or derivatives thereof, and/or trehalose. The amide containing amino acids can, for example, be selected from the group consisting of asparagine, glutamine, derivatives thereof, or combinations thereof. For example, the amide-containing amino acids may include natural forms of asparagine, anhydrous asparagine, asparagine monohydrate, or natural forms of glutamine, anhydrous glutamine, and/or glutamine monohydrate, each in the form of the L-isomer or D-isomer.

The concentration of the amide containing amino acids or derivatives thereof in the medium can vary depending upon the desired end result of the culture. For example, a culture may be carried out for the purpose of producing microorganisms having a specific enzymatic activity. Optionally, a culture may be carried out for the purpose of forming and collecting a specific enzyme from the cultured microorganisms. Optionally, a culture may be carried out for the purpose of forming and collecting a plurality of enzymes having the same or different activities and functions.

The amount of the amide containing amino acids, or derivatives thereof, added to the growth medium or mixture can generally be up to 10,000 parts per million (ppm) (i.e., 1% by weight) based on the overall weight of the medium or mixture. The induction methods are particularly beneficial, however, in that enzyme activity can be induced through addition of even lesser amounts. Optionally, the one or more amide containing amino acids are present at a concentration of at least 50 ppm. By way of other examples, the concentration of the amide containing amino acids or derivatives thereof is in the range of 50 ppm to 5,000 ppm, 100 ppm to 3,000 ppm, 200 ppm to 2,000 ppm, 250 ppm to 1500 ppm, 500 ppm to 1250 ppm, or 500 ppm to 1000 ppm.

In some embodiments, the stabilization methods include the use of trehalose. The concentration of trehalose in the compositions or medium used in the induction methods can be at least 1 gram per liter (g/L). Optionally, the concentration of trehalose is in the range of 1 g/L to 50 g/L, or 1 g/L to 10 g/L. Optionally, the concentration of trehalose in the medium is at least 4 g/L.

The amide containing amino acids or derivatives thereof and/or trehalose are added to a nutritionally complete media. A suitable nutritionally complete medium generally is a growth medium that can supply a microorganism with the necessary nutrients required for its growth, which minimally includes a carbon and/or nitrogen source. One specific example is the commercially available R2A agar medium, which typically consists of agar, yeast extract, proteose peptone, casein hydrolysate, glucose, soluble starch, sodium pyruvate, dipotassium hydrogenphosphate, and magnesium sulfate. Another example of a nutritionally complete liquid medium is Yeast Extract Malt Extract Agar (YEMEA), which consists of glucose, malt extract, and yeast extract (but specifically excludes agar). Also, media of similar composition, but of vegetable origin can be used for the disclosed methods. Any nutritionally complete medium known in the art could be used for the disclosed methods, the above media being described for exemplary purposes only. Such nutritionally complete media can be included in the compositions described herein.

Optionally, the disclosed compositions and media can contain further additives. Typically, the other supplements or nutrients are those useful for assisting in greater cell growth, greater cell mass, or accelerated growth. For example, the compositions and media can comprise a carbohydrate source in addition to any carbohydrate source already present in the nutritionally complete medium.

As described above, most media typically contain some content of carbohydrate (e.g., glucose); however, it can be useful to include an additional carbohydrate source (e.g., maltose or less refined sugars, such as dextrose equivalents that would be polymers of dextrose, or compositions such as molasses or sorghum, or any carbohydrate that supports growth of the cell and induction of the desired activity). The type of excess carbohydrate provided can depend upon the desired outcome of the culture. For example, the addition of carbohydrates, such as maltose or maltodextrin, has been found to provide improved induction of asparaginase I. Additionally, the addition of carbohydrates, such as maltose or maltodextrin, potentially improves stability of enzymatic activity (e.g., nitrile hydratase activity).

In some embodiments, the compositions and media further comprise cobalt. Cobalt or a salt thereof can be added to the mixture or media. For example, the addition of cobalt (e.g., cobalt chloride) to the media can be particularly useful for increasing the mass of the enzyme produced by the cultured microorganisms. Cobalt or a salt thereof can, for example, be added to the culture medium such that the cobalt concentration is an amount up to 400 ppm. Cobalt can, for example, be present at a concentration of 5 ppm to 400 ppm, 10 ppm to 100 ppm, 10 ppm to 80 ppm, or 10 ppm to 25 ppm.

In some embodiments, the compositions and media further comprise urea. Urea or a salt thereof can be added to the mixture or media. Urea or a salt thereof can, for example, be added to the culture medium such that the urea concentration is in an amount up to 10 g/L. Urea can, for example, be present in a concentration of 5 g/L to 30 g/L, 5 g/L to 20 g/L, 5 g/L to 12 g/L, or 7 g/L to 10 g/L. Optionally, urea is present at a concentration of 7.5 g/L. Optionally, both urea and cobalt are added to the media.

The compositions and media may also include further components. For example, other suitable medium components may include commercial additives, such as cottonseed protein, maltose, maltodextrin, and other commercial carbohydrates. Optionally, the medium further comprises maltose or maltodextrin. Maltose or maltodextrin, for example, can be added to the culture medium such that the maltose or maltodextrin concentration is at least 1 g/L. Optionally, the compositions and media are free of any nitrile containing compounds. Nitrile compounds were previously required in the culture medium to induce enzyme activity toward two or more nitrile compounds. The compositions described herein achieve this through the use of completely safe trehalose and/or amide containing amino acids or derivatives thereof; therefore, the medium can be free of any nitrile containing compounds.

"Enzymatic activity," as used herein, generally refers to the ability of an enzyme to act as a catalyst in a process, such as the conversion of one compound to another compound. Likewise, the desired activity referred to herein can include the activity of one or more enzymes being actively expressed by one or more microorganisms. In particular, nitrile hydratase catalyzes the hydrolysis of nitrile (or cyanohydrin) to the corresponding amide (or hydroxy acid). Amidase catalyzes the hydrolysis of an amide to the corresponding acid or hydroxy acid. Similarly, an asparaginase enzyme, such as asparaginase I, catalyzes the hydrolysis of asparagine to aspartic acid. ACC deaminase catalyzes the hydrolysis of 1-aminocyclopropane-1-carboxylate to ammonia and α-ketobutyrate. Beta-cyanoalanine synthase catalyzes the formation of the non-protein amino acid cyanoalanine from cysteine and cyanide. Cyanidase catalyzes the hydrolysis of cyanide to ammonia and formate. Monooxygenases such as for example, alkane, alkene, or ammonium monooxygenase and methane monooxygenase that can catalyze the hydrolysis of ethylene to ethylene epoxide. Toluene dioxygenase can, for example, oxidize ethylene, and is known as an AMO-like enzyme. Ethylene degradation activity results in the degradation of produced ethylene.

Activity can be referred to in terms of "units" per mass of enzyme or cells (typically based on the dry weight of the cells, e.g., units/mg cdw). A "unit" generally refers to the ability to convert a specific content of a compound to a different compound under a defined set of conditions as a function of time. Optionally, one "unit" of nitrile hydratase activity refers to the ability to convert 1 μmol of acrylonitrile to its corresponding amide per minute, per milligram of cells (dry weight) at a pH of 7.0 and a temperature of 30° C. Similarly, one unit of amidase activity refers to the ability to convert 1 μmol of acrylamide to its corresponding acid per minute, per milligram of cells (dry weight) at a pH of 7.0 and a temperature of 30° C. Further, one unit of asparaginase I activity refers to the ability to convert 1 μmol of asparagine to its corresponding acid per minute, per milligram of cells (dry weight) at a pH of 7.0 and a temperature of 30° C. Further, one unit of ACC deaminase activity refers to the ability to convert 1 μmol of 1-aminocyclopropane-1-carboxylate to ammonia and α-ketobutyrate per minute, per milligram of cells (dry weight) at a pH of 7.0 and a temperature of 30° C. Further, one unit of cyanoalanine synthase-like enzyme activity refers to the ability to convert 1 μmol of cysteine and cyanide to cyanoalanine per minute, per milligram of cells (dry weight) at a pH of 7.0 and a temperature of 30° C. Further, one unit of cyanidase activity refers to the ability to convert 1 μmol of cyanide to ammonia and formate per minute, per milligram of cells (dry weight) at a pH of 7.0 and a temperature of 30° C. Further, one unit of alkane or ammonium monooxygenase (AMO) or methane monooxygenase activity refers to the ability to convert 1

µmol of ethylene to ethylene epoxide. Further, one unit of toluene dioxygenase refers to the ability to convert 1 µmol of ethylene to ethylene epoxide. Assays for measuring nitrile hydratase activity, amidase activity, asparaginase activity, ACC deaminase activity, cyanoalanine synthase-like enzyme activity, Monooxygenases such as for example, alkane, alkene, or ammonium monooxygenase activity, methane monooxygenase activity, EDTA-monooxygenase, or NTA-monooxygenase, and cyanidase activity are known in the art and include, for example, the detection of free ammonia. See, e.g., Fawcett and Scott, J. Clin. Pathol. 13:156-9 (1960).

In some cases, any bacterial, fungal, plant, or animal cell capable of producing or being induced to produce nitrile hydratase, amidase, asparaginase, ACC deaminase activity, cyanoalanine synthase-like enzyme activity, alkane or ammonium monooxygenase (AMO) activity, methane monooxygenase activity, toluene dioxygenase activity, and cyanidase activity, or any combination thereof may be used herein. A nitrile hydratase, amidase, asparaginase, ACC deaminase, cyanoalanine synthase-like enzyme, alkane or ammonium monooxygenase, methane monooxygenase, toluene dioxygenase, and/or cyanidase may be produced constitutively in a cell from a particular organism (e.g., a bacterium, fungus, plant cell, or animal cell) or, alternatively, a cell may produce the desired enzyme or enzymes only following "induction" with a suitable inducing agent. "Constitutively" is intended to mean that at least one enzyme disclosed herein is continually produced or expressed in a particular cell type. Other cell types, however, may need to be "induced," as described above, to express nitrile hydratase, amidase, asparaginase, ACC deaminase, cyanoalanine synthase-like enzyme, alkane or ammonium monooxygenase, methane monooxygenase, toluene dioxygenase, and cyanidase at a sufficient quantity or enzymatic activity level to fungal growth. That is, an enzyme disclosed herein may only be produced (or produced at sufficient levels) following exposure to or treatment with a suitable inducing agent. Such inducing agents are known and outlined above. For example, the one or more bacteria are treated with an inducing agent such as urea, methyl carbamate, cobalt, asparagine, glutamine, or any mixture thereof, more particularly urea or methyl carbamate optionally in combination with asparagine or cobalt. Furthermore, as disclosed in U.S. Pat. Nos. 7,531,343 and 7,531,344, which are incorporated by reference in their entireties, entitled "Induction and Stabilization of Enzymatic Activity in Microorganisms," asparaginase I activity can be induced in *Rhodococcus rhodochrous* DAP 96622 (Gram-positive) or *Rhodococcus rhodochrous* DAP 96253 (Gram-positive), in medium supplemented with amide containing amino acids or derivatives thereof. Other strains of *Rhodococcus* can also preferentially be induced to exhibit asparaginase I enzymatic activity utilizing amide containing amino acids or derivatives thereof.

*P. chloroaphis* (ATCC Deposit No. 43051), which produces asparaginase I activity in the presence of asparagine and ACC deaminase, and *B. kletoglutamicum* (ATCC Deposit No. 21533), a Gram-positive bacterium that has also been shown to produce asparaginase activity, are also used in the disclosed methods. Fungal cells, such as those from the genus *Fusarium*, plant cells, and animal cells, that express a nitrile hydratase, amidase, and/or an asparaginase, may also be used herein, either as whole cells or as a source from which to isolate one or more of the above enzymes.

The nucleotide and amino acid sequences for several nitrile hydratases, amidases, and asparaginases (e.g., type I asparaginases) from various organisms are disclosed in publicly available sequence databases. A non-limiting list of representative nitrile hydratases and aliphatic amidases known in the art is set forth in Tables 1 and 2 and in the sequence listing. The "protein score" referred to in Tables 1 and 2 provide an overview of percentage confidence intervals (% Confid. Interval) of the identification of the isolated proteins based on mass spectroscopy data.

TABLE 1

Amino Acid Sequence Information for Representative Nitrile Hydratases

| Source organism | Accession No. | Sequence Identifier | Protein Score (% Confid. Interval) |
| --- | --- | --- | --- |
| *Rhodococcus* sp. | 806580 | SEQ ID NO: 1 | 100% |
| *Nocardia* sp. | 27261874 | SEQ ID NO: 2 | 100% |
| *Rhodococcus rhodochrous* | 49058 | SEQ ID NO: 3 | 100% |
| Uncultured bacterium (BD2); beta-subunit of nitrile hydratase | 27657379 | SEQ ID NO: 4 | 100% |
| *Rhodococcus* sp. | 806581 | SEQ ID NO: 5 | 100% |
| *Rhodococcus rhodochrous* | 581528 | SEQ ID NO: 6 | 100% |
| Uncultured bacterium (SP1); alpha-subunit of nitrite hydratase | 7657369 | SEQ ID NO: 7 | 100% |

TABLE 2

Amino Acid Sequence Information for Representative Aliphatic Amidases

| Source organism | Accession No. | Sequence Identifier | Protein Score (% Confid. Interval) |
| --- | --- | --- | --- |
| *Rhodococcus rhodochrous* | 62461692 | SEQ ID NO: 8 | 100% |
| *Nocardia farcinica* IFM 10152 | 54022723 | SEQ ID NO: 9 | 100% |
| *Pseudomonas aeruginosa* PAO1 | 15598562 | SEQ ID NO: 10 | 98.3% |
| *Helicobacter pylori* J99 | 15611349 | SEQ ID NO: 11 | 99.6% |
| *Helicobacter pylori* 26695 | 2313392 | SEQ ID NO: 12 | 97.7% |
| *Pseudomonas aeruginosa* | 150980 | SEQ ID NO: 13 | 94% |

Optionally, host cells that have been genetically engineered to express a nitrile hydratase, amidase, asparaginase, ACC deaminase, cyanoalanine synthase-like enzyme, alkane monooxygenase, toluene dioxygenase, and/or cyanidase can be exposed to a location for inhibiting or reducing fungal growth or development of fungal growth. Specifically, a polynucleotide that encodes a nitrile hydratase, amidase, asparaginase, ACC deaminase, cyanoalanine synthase-like enzyme, alkane or ammonium monooxygenase, methane monooxygenase, toluene dioxygenase, or cyanidase (or multiple polynucleotides each of which encodes a nitrile hydratase, amidase, asparaginase, ACC deaminase, cyanoalanine synthase-like enzyme, alkane or ammonium monooxygenase, methane monooxygenase, toluene dioxygenase, or cyanidase) may be introduced by standard molecular biology techniques into a host cell to produce a transgenic cell that expresses one or more of the enzymes. The use of the terms "polynucleotide," "polynucleotide construct," "nucleotide," or "nucleotide construct" is not intended to limit to polynucleotides or nucleotides comprising DNA. Those of ordinary skill in the art will recognize that polynucleotides and nucleotides can comprise ribonucleotides and combinations of ribonucleotides and deoxyribonucleotides. Such deoxyribonucleotides and ribonucleotides include both naturally occurring molecules and synthetic analogues. The polynucleotides described herein encompass all forms of sequences including, but not limited to, single-stranded forms, double-stranded forms, and the like.

Variants and fragments of polynucleotides that encode polypeptides that retain the desired enzymatic activity (i.e., nitrile hydratase, amidase, asparaginase, ACC deaminase, cyanoalanine synthase-like enzyme, alkane or ammonium monooxygenase, methane monooxygenase, toluene dioxygenase, or cyanidase activity) may also be used herein. By "fragment" is intended a portion of the polynucleotide and hence also encodes a portion of the corresponding protein. Polynucleotides that are fragments of an enzyme nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length enzyme polynucleotide sequence. A polynucleotide fragment will encode a polypeptide with a desired enzymatic activity and will generally encode at least 15, 25, 30, 50, 100, 150, 200, or 250 contiguous amino acids, or up to the total number of amino acids present in a full-length enzyme amino acid sequence. "Variant" is intended to mean substantially similar sequences. Generally, variants of a particular enzyme sequence will have at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the reference enzyme sequence, as determined by standard sequence alignment programs. Variant polynucleotides described herein will encode polypeptides with the desired enzyme activity. By way of example, the relatedness between two polynucleotides or two polypeptides can be described as identity. The identity between two sequences can be determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-7). The output of Needle labeled "longest identity" is used as the percent identity and is calculated as (Identical Residues (i.e., nucleotides or peptides)×100)/ (Length of Alignment−Total Number of Gaps in Alignment).

As used in the context of production of transgenic cells, the term "introducing" is intended to mean presenting to a host cell, particularly a microorganism such as *Escherichia coli*, with a polynucleotide that encodes a nitrile hydratase, amidase, asparaginase, ACC deaminase, cyanoalanine synthase-like enzyme, alkane or ammonium monooxygenase, methane monooxygenase, toluene dioxygenase, and/or cyanidase. Optionally, the polynucleotide will be presented in such a manner that the sequence gains access to the interior of a host cell, including its potential insertion into the genome of the host cell. The disclosed methods do not depend on a particular protocol for introducing a sequence into a host cell, only that the polynucleotide gains access to the interior of at least one host cell. Methods for introducing polynucleotides into host cells are well known, including, but not limited to, stable transfection methods, transient transfection methods, and virus-mediated methods. "Stable transfection" is intended to mean that the polynucleotide construct introduced into a host cell integrates into the genome of the host and is capable of being inherited by the progeny thereof "Transient transfection" or "transient expression" is intended to mean that a polynucleotide is introduced into the host cell but does not integrate into the host's genome.

Furthermore, the nitrile hydratase, amidase, asparaginase, ACC deaminase, cyanoalanine synthase-like enzyme, monooxygenases such as for example, alkane, alkene, or ammonium monooxygenase, methane monooxygenase, toluene dioxygenase, or cyanidase nucleotide sequence may be contained in, for example, a plasmid for introduction into the host cell. Typical plasmids of interest include vectors having defined cloning sites, origins of replication, and selectable markers. The plasmid may further include transcription and translation initiation sequences and transcription and translation terminators. Plasmids can also include generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optimally both. For general descriptions of cloning, packaging, and expression systems and methods, see Giliman and Smith, Gene 8:81-97 (1979); Roberts et al., *Nature* 328:731-734 (1987); Berger and Kimmel, Guide to Molecular Cloning Techniques, Methods in Enzymology, Vol. 152 (Academic Press, Inc., San Diego, Calif.) (1989); Sambrook et al., Molecular Cloning: A Laboratory Manual, Vols. 1-3 (2d ed; Cold Spring Harbor Laboratory Press, Plainview, N.Y.) (1989); and Ausubel et al., Current Protocols in Molecular Biology, Current Protocols (Greene Publishing Associates, Inc., and John Wiley & Sons, Inc., New York; 1994 Supplement) (1994). Transgenic host cells that express one or more of the enzymes may be used in the disclosed methods as whole cells or as a biological source from which one or more enzymes can be isolated.

Apparatuses and carriers for inhibiting or reducing fungal growth and for performing the methods disclosed are further provided. In particular embodiments, an apparatus or carrier for inhibiting or reducing fungal growth comprising a catalyst that comprises one or more bacteria selected from the group consisting of *Rhodococcus* spp., *Pseudomonas chloroaphis, Brevibacterium ketoglutamicum*, and mixtures thereof is disclosed herein. *Rhodococcus rhodochrous* DAP 96253 strain, *Rhodococcus rhodochrous* DAP 96622 strain, *Rhodococcus erythropolis*, or mixtures thereof may be used in certain aspects. The one or more bacteria of an apparatus or carrier are provided in a quantity sufficient to inhibit or reduce fungal growth as defined herein above. In other aspects, the catalyst comprises one or more enzymes (i.e., nitrile hydratase, amidase, asparaginase, ACC deaminase, cyanoalanine synthase-like enzyme, alkane or ammonium monooxygenase, methane monooxygenase, toluene dioxygenase, and/or cyanidase) in a quantity or at an enzymatic activity level sufficient to inhibit or reduce fungal growth. Sources of the desired enzymes for use as a catalyst in the apparatuses or carriers disclosed herein are also described in detail above. For example, the catalyst may be used in the form of whole cells that produce (or are induced or genetically modified to produce) one or more of the enzymes or may comprise the enzyme(s) themselves in an isolated, purified, or semi-purified form. A carrier for compositions for inhibiting or reducing fungal growth can, for example, be selected from the group consisting of paper, DEAE, cellulose, waxes, glutaraldehyde, and granular activated carbon.

Apparatuses for inhibiting or reducing fungal growth encompassed by the present disclosure may be provided in a variety of suitable formats and may be appropriate for single use or multiple uses (e.g., "re-chargeable"). In particular embodiments, the catalyst is provided in an immobilized format. Any process or matrix for immobilizing the catalyst may be used so long as the ability of the one or more bacteria (or enzymes) to inhibit or reduce fungal growth is retained. For example, the catalyst may be immobilized in a matrix comprising alginate (e.g., calcium alginate), carrageenan, DEAE-cellulose, or polyacrylamide. Other such matrices are well known in the art and may be further cross-linked with any appropriate cross-linking agent, including but not limited to glutaraldehyde and/or polyethylenimine, to increase the mechanical strength of the catalyst matrix. In one aspect, the catalyst is immobilized in a glutaraldehyde cross-linked DEAE-cellulose matrix. The catalyst, particularly the catalyst in an immobilized form, may be further presented as a "catalyst module element." A catalyst module element comprises a catalyst, such as an immobilized catalyst, within an additional structure that, for example, reduces potential contact with the catalyst, facilitates replacement of the catalyst, or permits air flow across the catalyst.

In some embodiments, the matrix comprises alginate, or salts thereof. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. In one embodiment, calcium alginate is used as the substrate, more particularly calcium alginate that has been cross-linked, such as with polyethylenimine, to form a hardened calcium alginate substrate. Further description of such immobilization techniques can be found in Bucke (1987) "Cell Immobilization in Calcium Alginate" in *Methods in Enzymology*, Vol. 135(B) (Academic Press, Inc., San Diego, Calif.; Mosbach, ed.), which is incorporated herein by reference. An exemplary method of immobilization using polyethylenimine cross-linked calcium alginate is also described below in Example 5. In another embodiment, the matrix comprises an amide-containing polymer. Any polymer comprising one or more amide groups could be used. In one embodiment, the substrate comprises a polyacrylamide polymer.

Increased mechanical strength of an immobilized catalyst matrix can be achieved through cross-linking. For example, cells can be chemically cross-linked to form agglutinations of cells. In one embodiment, cells harvested are cross-linked using glutaraldehyde. For example, cells can be suspended in a mixture of de-ionized water and glutaraldehyde followed by addition of polyethylenimine (PEI) until maximum flocculation is achieved. The cross-linked cells (typically in the form of particles formed of a number of cells) can be harvested by simple filtration. Further description of such techniques is provided in Lopez-Gallego et al. (2005) *J. Biotechnol.* 119:70-75, which is hereby incorporated by reference in its entirety.

In certain aspects, the immobilized catalyst or one or more catalyst module elements are placed in, placed on, or affixed to a "physical structure." The physical structure includes but is not limited to a film, sheet, coating layer, box, pouch, bag, or slotted chamber capable of holding one or more catalyst module elements. The physical structure may further comprise more than one individual structure, whereby all of the individual structures are connected to a central catalyst or catalyst module element.

The skilled artisan will further recognize that any of the methods, apparatuses, physical structures, compositions, or carriers disclosed herein can be combined with other known methods, apparatuses, physical structures, compositions, and carriers for inhibiting or reducing fungal growth. Moreover, as described above, increased ethylene production has also been observed during attack of plants or plant parts by pathogenic organisms. Accordingly, the methods and apparatuses disclosed herein may find further use in improving plant response to pathogens.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1: Bacterially-Mediated Contact-Independent Antagonism of Fungal Diseases of Bats and Honeybees One out of three bites of food come from a bee-pollinated plant, and nearly ⅓ of all honey bee colonies in the U.S. have vanished. Chalkbrood is a fungal disease caused by *Ascosphaera apis* that infests the gut of honey bee larva. The fungus competes with the larva for food, ultimately causing it to starve. The fungus will then go on to consume the rest of the larva's body, causing it to appear white and chalky.

Stonebrood is a fungal disease caused by *Aspergillus fumigatus, Aspergillus flavus*, and *Aspergillus niger*. It causes mummification of the brood of a honey bee colony. The fungi are common soil inhabitants and are also pathogenic to other insects, birds, and mammals. The disease is difficult to identify in the early stages of infection. The spores of the different species have different colors and can also cause respiratory damage to humans and other animals. When a bee larva injests spores, the germination of these spores in the gut results in rapid growth growing rapidly to form a collar-like ring near the head. After death, the larvae turn black and become difficult to crush, hence the name stonebrood. Eventually, the fungus erupts from the integument of the larva and forms a false skin. In this stage, the larvae are covered with powdery fungal spores. Worker bees clean out the infected brood and the hive may recover depending on factors such as the strength of the colony, the level of infection, and hygienic habits of the strain of bees (there is variation in the trait among different subspecies/races).

White-nose syndrome (WNS) is a fungal disease associated with the deaths of at least 5.7 million to 6.7 million North American bats. The condition, named for a distinctive fungal growth around the muzzles and on the wings of hibernating bats, was first identified in a cave in Schoharie County, N.Y., in February 2006. It has rapidly spread, and as of 2013, the condition had been found in over 115 caves and mines ranging mostly throughout the Northeastern U.S. and as far south as Alabama and west to Missouri and into four Canadian provinces. It is believed that *Pseudogymnoascus destructans* (formerly *Geomyces destructans*) is the sole cause of the disease. No treatment or means of preventing transmission is available, and the mortality rate of some species has been observed at 95%. WNS and the increased development of wind-power facilities are threatening populations of insectivorous bats in North America. Bats are voracious predators of nocturnal insects, including many crop and forest pests. There is evidence that loss of bats in North America could lead to agricultural losses estimated at more than $3.7 billion/year (Boyles et al. *Science* 2011 332(6025):41-42). Urgent efforts are needed to educate the public and policy-makers about the ecological and economic importance of insectivorous bats and to provide practical conservation solutions.

Figure 1B:
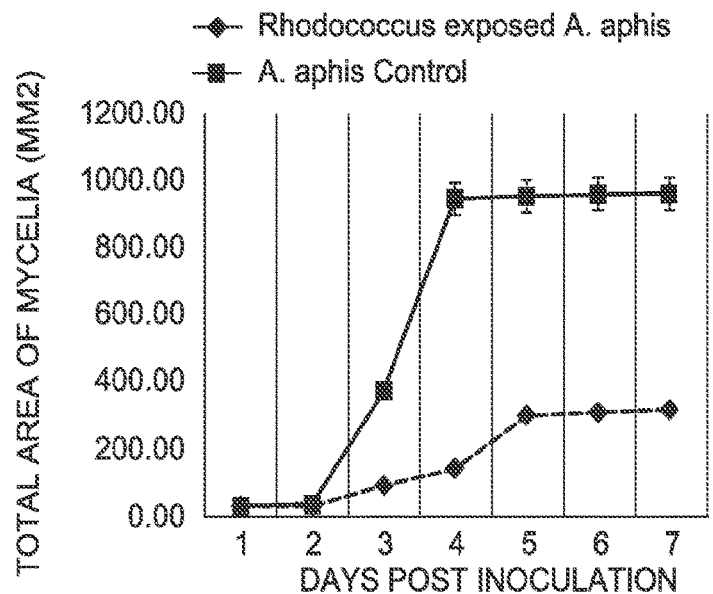
Figure 2A:
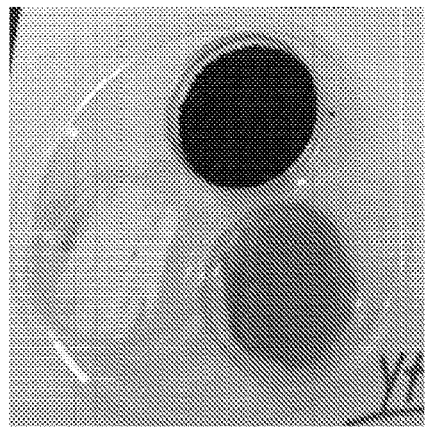
FIG. 2 is an image of culture dishes showing the antifungal activity of *Rhodococcus rhodochrous* DAP 96253 is abolished in the presence of activated carbon.
Figure 2B:
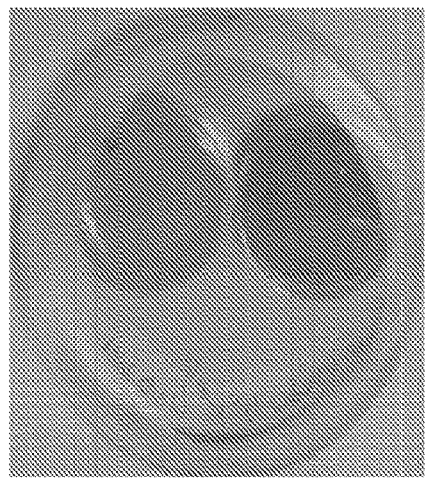
Figure 2C:
Figure 4A:
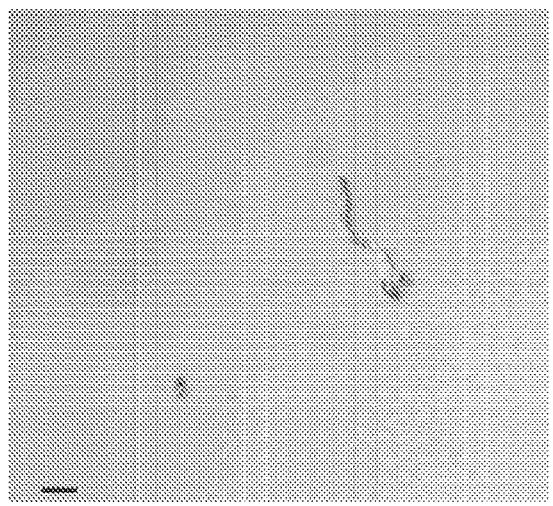
FIG. 4 is a series of images showing *Rhodococcus rhodochrous* DAP 96253 controls *Pseudogymnoascus destructans* spore germination. Experiment conducted at 15° C. All images captured at 200× magnification. Scale bar is 10 µm.
Figure 4B:
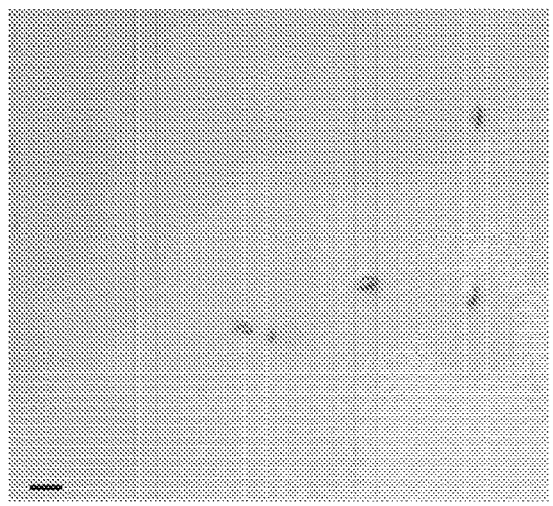
Figure 4C:
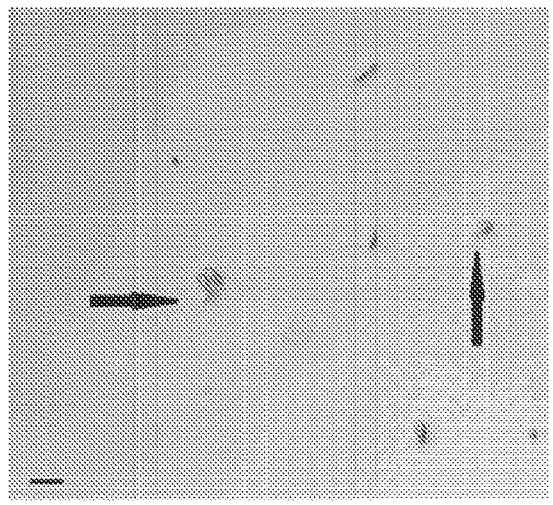
Figure 5A:
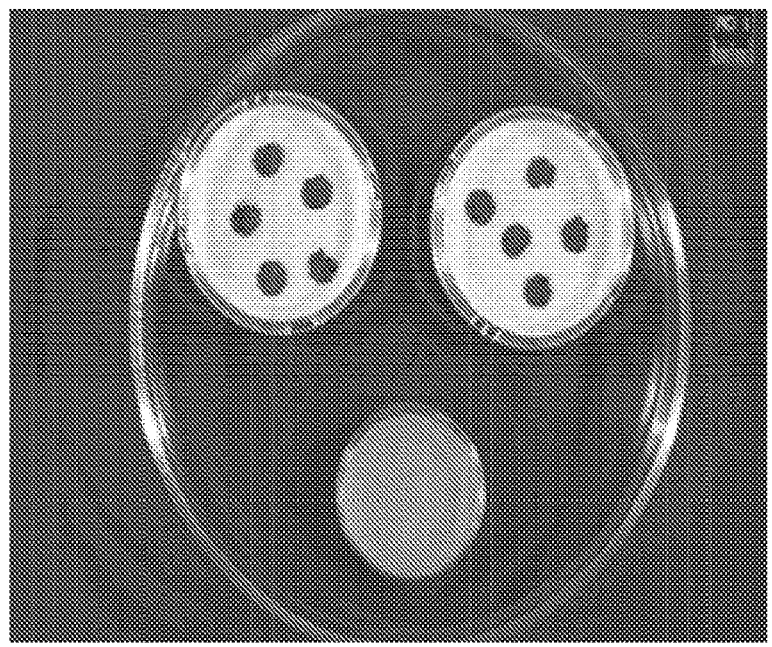
FIGS. 5A and 5B are images showing Explants inoculated with ~100 *P. destructans* conidia each and incubated with induced *Rhodococcus* at 7° C. for 40 days. No exposed explants developed any fungal colonization over 21 days. All controls were fully colonized by day 14.
Figure 5B:
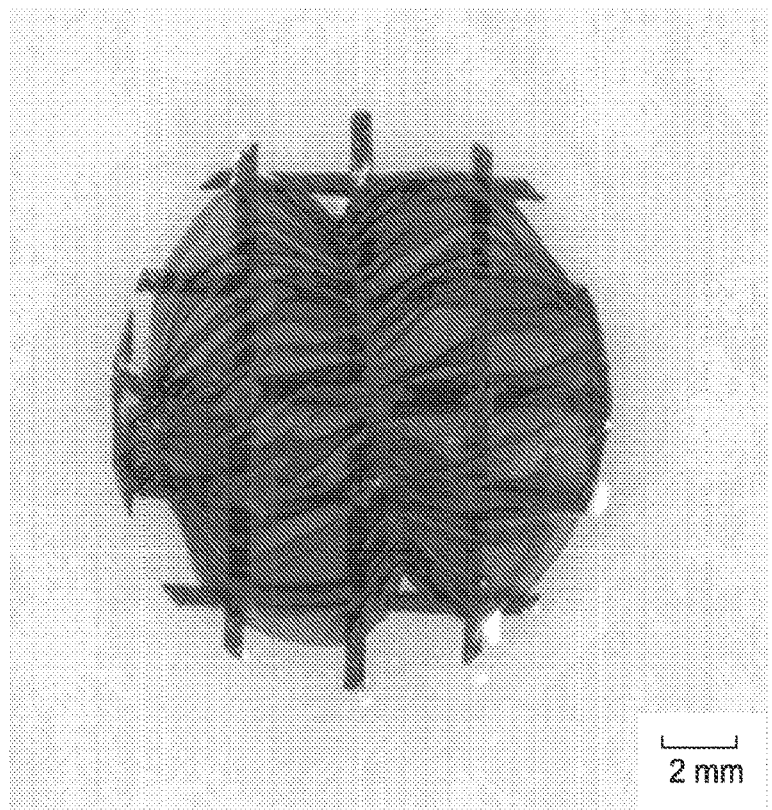
Figure 7A:
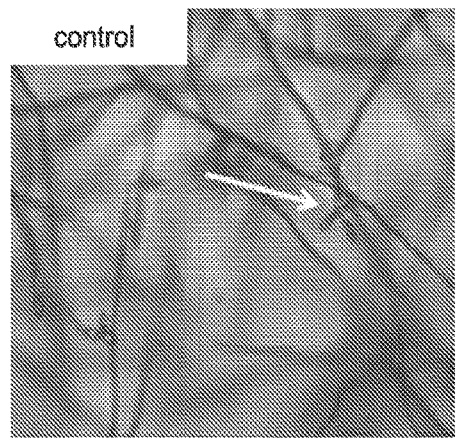
FIG. 7 is a series of images showing permanent inhibition of spore germination 0 hours, 24 hours, 72 hours, or 7 days after exposure to *Rhodococcus*.
Figure 7B:
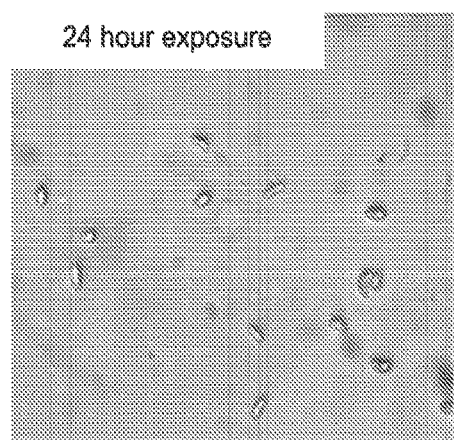
Figure 7C:
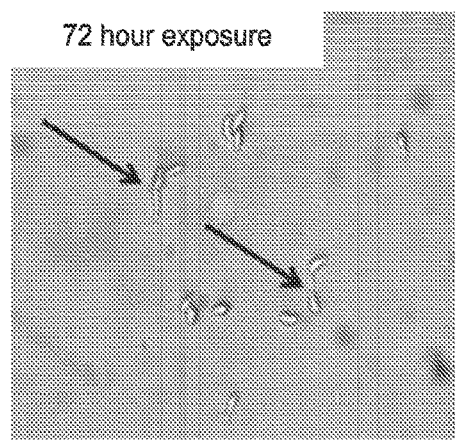
Figure 7D:
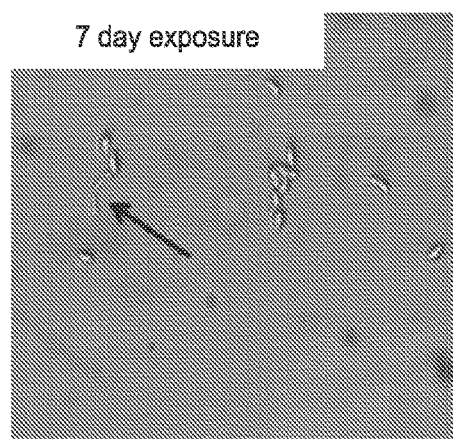
Figure 8A:
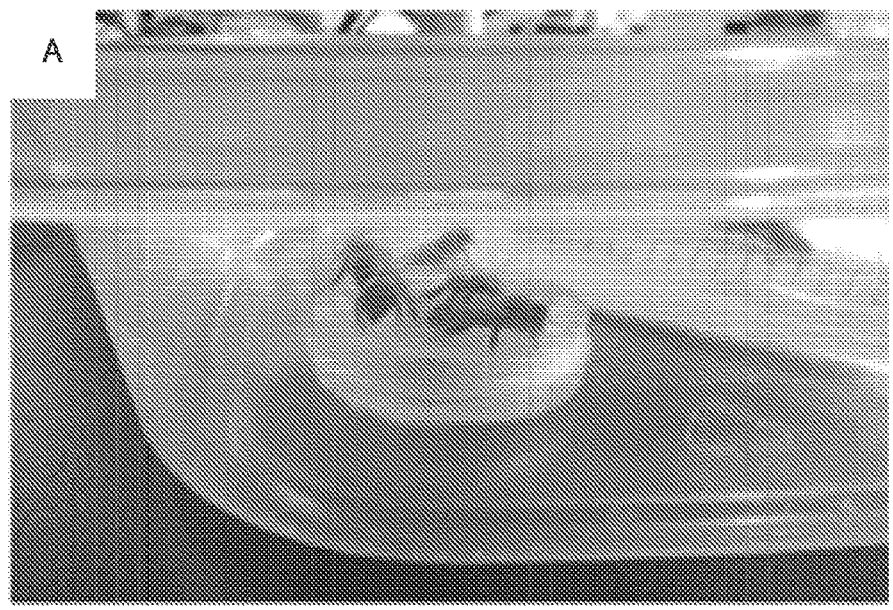
FIGS. 8A and 8B are images showing *Rhodococcus* has no contact or oral toxicity to adult Honey Bees.
Figure 8B:
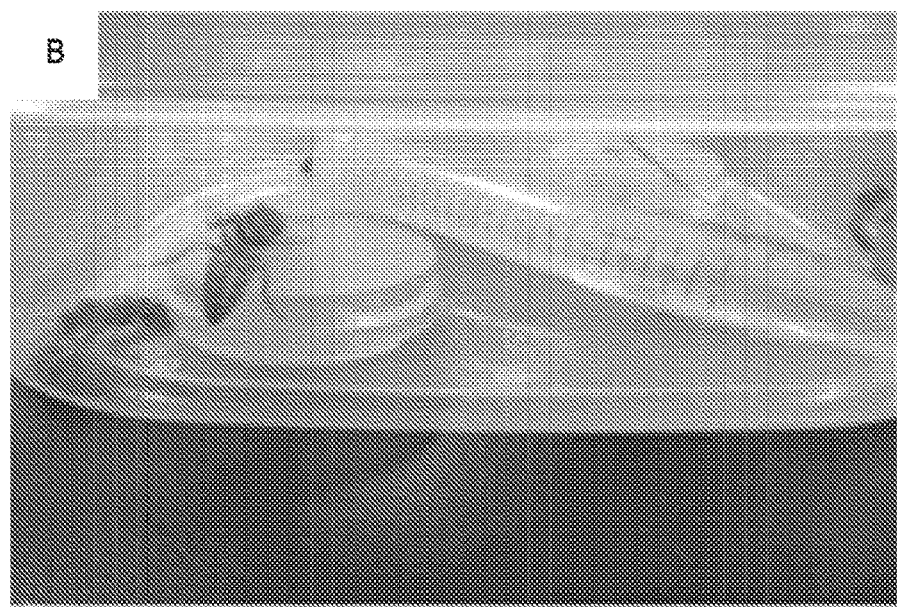

Experiments were conducted to evaluate *Rhodococcus rhodochrous* DAP 96253 for contact-independent antagonism of *P. destructans* and *A. apis*. FIGS. 5A and 5B show that induced cells of *Rhodococcus rhodochrous* DAP 96253 is an effective biological control agent for *P. destructans* (FIG. 1A) and *A. apis* (FIG. 1B). This anti-fungal activity is abolished in the presence of activated carbon (FIG. 2). FIG. 3 shows SPME-GC-MS headspace analysis of uninduced (top) and induced (bottom) *Rhodococcus*.

Induced cells of *Rhodococcus rhodochrous* DAP 96253 halts *Pseudogymnoascus destructans* spore germination (FIG. 4) and prevents *P. destructans* fungal colonization ex vivo in explants (FIG. 5). Moreover, this effect is contact-independent (FIG. 6) and permanent (FIG. 7).

As shown in FIG. 8 and the Table 7, induced cells of *Rhodococcus* has no contact or oral toxicity to adult Honey Bees.

TABLE 7

| Contact Toxicity in Honey Bees | | | | | | |
|---|---|---|---|---|---|---|
| Contact toxicity | 0 | 24 | 48 | 72 | 96 | 120 |
| Dimethoate control | 0.00% | 76.00% | 86.00% | 90.00% | 92.00% | 94.00% |
| Untreated | 0.00% | 0.00% | 0.00% | 2.00% | 2.00% | 2.00% |
| Plate exposed | 0.00% | 0.00% | 0.00% | 0.00% | 0.00% | 2.00% |
| Paste exposed | 0.00% | 0.00% | 0.00% | 0.00% | 0.00% | 0.00% |

Likewise, healthy, torpid, and euthermic bats had no observable negative reactions to induced *Rhodococcus*. Neither exposed or control groups had any mortality in an in vitro trial.

Therefore, induced cells of *R. rhodochrous* can be used to treat and prevent fungal infection in bees and bats. Commercial bees can be treated by the application of the catalyst to the colony through incorporation of the catalyst in the hive matrix or through water, etc. The inoculation of wild, native bees presents more of a problem. However, by incorporating the catalyst (live or dead) into a "partially-sticky" small particle, bees that are attracted to a bait/simulant will pick up the particles. Upon their return to the hive, the bees can be groomed by other bees in the colony, resulting in the inoculation of the colony. For example, the partially sticky material can be similar to the microbeads/nanobeads that are used in "sticky-notes".

The catalyst can also be incorporated into wax/wax-like materials and structures. Induced cells of *R. rhodochrous* DAP 96253 have been incorporated into wax(es) that can then be applied to fruit (by spray, soak, dip, etc.) or applied to (or incorporated into the structure) packing boxes/containers. Such applications showed both delayed ripening and mold inhibition. Example waxes that can be used include petroleum, animal, insect, or vegetable based waxes and/or wax emulsions. Based upon this, the catalyst could be incorporated into wax (such as beeswax) to make "authentic" wax structures in the hive or alternatively into other wax, waxes, or wax compositions to present the catalyst to bees in the hive.

A number of the bats infected with *P. destructans* and exposed to induced cells of *R. rhodochrous* DAP 96253 exhibited hybernacular behavior typical of normal hibernating bats, whereas, infected bats in the control group exhibited behavior indicative of the disease. The infected control bats also showed dehydration typically seen in diseased bats. Therefore it is possible to use the induced cell-*R. rhodochrous* derived catalyst to treat bats which carry the disease. However, induced cells of prepared *R. rhodochrous* DAP 96253 do not have to be in contact with bats or with *P. destructans* in order for the catalyst to inhibit or inhibit and kill the spores or propagules of *P. destructans*. Catalyst containing induced cell-*R. rhodochrous* can be configured such that the catalyst can be applied to areas of caves where hibernating bats reside, or presented as a substratum where bats can congregate. Furthermore the catalyst could be incorporated into bats/lures such that the bats bring the catalyst into the caves/hibernacula.

Example 2: In Vivo Evaluation of Fungistatic Volatile Compounds from Native Soil Bacteria *Rhodococcus rhodochrous*

Materials and Methods

Exposure Trial to Evaluate Toxicity (Toxicity Assessment): Collection, Sampling and Treatment Assignment Hibernating adult male *M. lucifugus* (n=18) were collected from a privately owned mine in Marion County, Mo. on 26 Jan. 2014. Each bat was swabbed to determine if Pd was present on their wing membrane or muzzles. After swabbing, each bat was placed individually in sterile cloth bags, and subsequently each bag was placed in an insulated container lined with damp towels to maintain high humidity and kept warm (25-30° C.) to reduce thermal stress while in transit. Bats were transported from the collection site to University of Missouri Columbia (UMC) where they were transferred to a BSL2 room and evaluated for mass (WT, g) (Acculab Pocket Pro 150-B, Edgewood, N.Y.) and forearm length (FA, mm) to assess body condition index (BCI; mass (g)/forearm length (mm)) Photos of each bat's wings were taken with illumination/transillumination of wing membranes using both natural light and long-wavelength UV light (360-385 nm) to check for fungal erosion fluorescence. Wing condition scores (WS) were also obtained.

The dehydration status (DS) of each bat was recorded using the following WNS Dehydration Scoring index:

0: No evidence of dehydration—skin immediately returns to normal position after tenting, eyes normal, mucous membranes pink and moist (0-5%)

1: Slight dehydration—wings slightly dry, slight delay in return of the skin to normal position, slight increase in CRT (6-8%).

2: Marginal dehydration—wings dry but not with wrinkled appearance, eyes slightly sunken, delay in return of the skin to normal position (8-10%).

3: Dehydrated—wings dry with slightly wrinkled appearance, eyes sunken, obvious delay in return of skin to normal (10-12%).

4: Serious dehydration—wings dry wrinkled appearance and rough in areas, eyes sunken, skin remains tented, signs of shock (>12%).

Each bat was uniquely marked with a lipped, numbered band (Porzana, Ltd, East Sussex, UK) and fitted with a custom-modified temperature sensitive data logger (iButtons, Model DS1922L, Thermocron, Baulkam Hills, NSW, Australia) to obtain skin temperatures ($T_{sk}$) every 30 minutes to evaluate time spent in torpor. Torpor was defined as $T_{sk}$ 10° C. or more below its highest temperature ($T_{max}$). Data loggers were attached by trimming a small patch of hair (interscapular) where the device was attached using a non-toxic adhesive (OstoBond, Montreal Ostomy, Quebec, Canada).

Animals were transferred randomly into nylon-mesh cages (n=2, 37×37×75 cm Apogee Reptarium™, Dallas, Tex., USA) with water and mealworms ad libitum and placed within a single hibernation chamber (Geneva Scientific Model I-36NL, Fontana, Wis., USA) maintaining a constant temperature of 7° C. and 95% relative humidity to acclimate to captivity and await results of swab analysis.

Due to concerns that Pd negative collection sites may no longer be available in Missouri, it was determined that individuals with very low levels of Pd would be allowed in the toxicity trials if they exhibited otherwise normal behavior. It was considered that low levels of Pd would represent bats at initial exposure to infection and with lowest potential for clinical WNS effects. Enclosures were equipped with infrared cameras (Nightowl, model CM115OH, Walpole, Mass., USA) and video recorders (Apollo, DVR5, Nightowl, Walpole, Mass., USA) to monitor bat behavior. Bats were visually inspected via camera up to 4 times daily and activity was automatically recorded if movement was sufficient to trigger camera.

Real-time PCR analysis for detection of Pd was conducted. All samples were run in duplicate and a sample was considered positive for Pd if either one of the runs detected Pd at a cycle threshold ($C_T$) less than 40. Real-time PCR detected low levels of Pd in 7 of the 18 individuals (mean $C_T$=38.7, range 37.4-39.9) and 2 also were lethargic during handling and were hanging singly during the acclimatization period. Since these 2 individuals were potentially exhibiting signs of clinical WNS, they were excluded from the toxicity assessment and held for subsequent treatment trials by placing them in a separate enclosure within the control group (NO RRDAP) chamber. A previous study found that disease transmission did not occur between infected and uninfected bats in the same chamber in separate enclosures with no physical contact between bats.

Chambers were opened for visual evaluation of bats, food and water replacement, and initiation of RRDAP exposure. The 5 individuals with low Pd values were randomly assigned to either the control group (n=3; NO RRDAP) or exposure group (n=2; RRDAP72) followed by the Pd negative bats (NO RRDAP n=5; RRDAP72 n=6). Blood samples were collected from randomly selected individuals (n=8; NO RRDAP n=4, RRDAP72 n=4) from the interfemoral vein to evaluate CBC and electrolytes for a concurrent study; fluid volume was replaced by equal quantity of lactated Ringers solution (LRS) to facilitate blood volume recovery. Bats were placed in mesh enclosures by treatment group and each enclosure was placed in an environmental chamber (n=2 chambers; Geneva Scientific Model I-36NL, Fontana, Wis., USA). Each chamber was maintained at 10° C. for 24 hours to allow bats to recover from blood sampling. Chambers were then lowered back to 7° C. and exposure to RRDAP initiated.

Behaviors of each group were evaluated by viewing all recordings and assigning behaviors to categories (Table 8) and whether clusters were maintained during non-active periods. Individual ID could not always be discerned so times in activities were calculated as total times for each group divided by number of bats in group per day of experiment and cumulative over the 26 day period.

TABLE 8

Codes for Bat Behavior Classifications

| CODE | ACTIVITY DESCRIPTION |
|---|---|
| A | Slight movement, bat hanging singly |
| B | Slight movement, bat hanging in cluster |
| C | Active movement, bat hanging singly -- grooming |
| D | Active movement, bat hanging in cluster -- grooming |
| E | Active movement, crawling or flying |
| F | Active movement, drinking |
| G | Active movement, in feed dish |

Toxicity Assessment: RRDAP Exposure

Induced *R. rhodochrous* DAP 96253 cells were supplied in sealed petri dishes. Dishes were placed on the floor of the RRDAP exposure chamber at approximately 1 g ft$^{-3}$ of total air volume. The NO RRDAP control chamber door was opened and closed without placing petri plates to simulate any potential disturbance associated with placing the RRDAP. Since 72 hours was the maximum level exposure to induced cells of *R. rhodochrous* DAP 96253 to be evaluated in subsequent treatment trials, the RRDAP was allowed to be in this chamber for 72 hours at which time the plates containing the induced cells of *R. rhodochrous* DAP 96253 were removed (RRDAP exposure group=RRDAP72). As with RRDAP placement in the treatment chamber, the door of the control chamber was also opened and closed to emulate conditions of the exposure group. Bats were visually inspected via camera at 4 hour intervals for the first 24 hours to watch for visible behavioral response to the exposure (i.e. rubbing of eyes or face or difficulty breathing). Starting day 2 visual inspections were at 4 hour intervals between 0700 and 1900 and cameras were checked each morning to determine if bats displayed behavior indicating distress during the night.

The two bats with potential symptoms of WNS were held untreated until Day 14; at that time all 18 bats were in good condition. Therefore, these 2 bats were treated for 24 hours by placing them in a small (13"×13"×13", Live Monarch Foundation, Boca Ratan, Fla.) enclosure within a 70 qt (2.33 cu ft) cooler (Coleman—Model 6270, Wichita, Kans., USA) and maintained at 10° C. and petri plates (100 mm) with congruent lawns of *R. rhodochrous* DAP 96253 were placed in the holding cooler at approximately 1 g ft-$^3$ of total air volume. After treatment they were placed in the VOC treatment chamber in a separate enclosure from the RRDAP72 treatment group.

Bats were maintained in separate chambers until day 26 when they were moved into a single chamber (Geneva Scientific Model AH-36VL, Fontana, Wis., USA) but maintained in separate enclosures to allow use of 2 identical chambers for treatment trials. Analyses of body condition and survival are based on the 26 day period they were maintained in separate chambers. Bats were maintained at 7° C. until Day 45 to determine if any developed WNS symptoms or visual fungus growth. At Day 45, chamber temperature was gradually increased to allow bats to transition to euthermic conditions in preparation for release. They were swabbed to determine Pd levels; those found negative for Pd were released at their site of capture.

Toxicity Assessment: Analysis

All analyses were performed in (SAS® 9.3, SAS Institute Inc., Allison 1995, SAS 2010). Differences in baseline health characteristics (WT, BCI, DS, WS) were tested for statistical significance using a mixed model approach to estimate treatment differences among repeatedly measured outcomes across the time range of the trial. The dependency in the data due to multiple observations per subject was accounted for using repeated measures in PROC MIXED. Means were compared ($\alpha=0.05$) at Day 1 and at approximately 10 day intervals by treatment and treatment*Pd status. Correlation between predictor variables was evaluated in PROC CORR.

Survival (OS) was estimated with non-parametric Kaplan-Meier models and difference in survival were tested with a log-rank test (PROC LIFETEST). Multivariate Cox proportional hazard models (CPHM) were fit to determine the effects of covariates (starting weight (SWT), BCI, WS, DS, $C_T$) on survival using maximum partial likelihood as computed in PROC PHREG. Bat mortality was expressed as a failure event and surviving bats at each interval were expressed as censored data. In the models, stratification was allowed for according to initial Pd status, in order to control for any variation in the shape of the hazard function between presence or absence of detectible conidia at trial onset. Omitting stratification, however, led to similar results. WT and BCI were modeled separately due to inherent correlation, (Pearson, r=0.90, p=<0.0001) and compared AIC of best model set.

Toxicity Assessment: Necropsy and Histopathology:

Bats not surviving the exposure trial (n=1) were evaluated for necropsy and histopathology.

*R. rhodochrous* DAP 96253 (RRDAP) Treatment Trial: Collection, Sampling and Treatment Assignment Sampling followed the methods of the toxicity assessment except that hibernating adult *M. lucifugus* (n=16; males=11, females=5) were collected from a cave in Franklin County, Mo. where bats had previously tested positive for Pd in 2012 and 2013. Each bat had visible signs of fungus on face, ears and/or forearms when collected. Bats were processed, transported and housed following the methods outlined for the toxicity assessment except that only water was allowed ad libitum; food was offered at each opening of the chambers and quantities consumed by each individual recorded to be used as an analysis covariate. Urine and feces were collected opportunistically for concurrent studies. As with the toxicity study, bats were allowed to acclimate to captivity prior to initiating treatments.

The chambers were opened for visual evaluation and weighing of bats, water replacement, feeding and initiation of treatment. Bats were randomly assigned to either the control group (n=8; NO RRDAP) or treatment group (n=8; RRDAP48). Females were randomly assigned first to ensure representation in both groups (RRDAP48 n=3; NO RRDAP n=2), and then males were randomly assigned (RRDAP48 n=5; NO RRDAP n=6). Blood samples were collected from the interfemoral vein to evaluate CBC and electrolytes for a concurrent study as in toxicity assessments.

RRDAP Treatment Trial: RRDAP Treatment

Non-growth cells of induced *R. rhodochrous* DAP96253 were supplied as cell paste in sealed container. Cell paste (27 gr, 1 g ft-3 chamber interior volume) was measured by weight into a sterile glass dish (Pyrex 8×10 units); the container of cell paste was placed on the floor of the RRDAP48 chamber. The door of the NO RRDAP chamber was sham opened without placing fermentation paste to simulate any potential disturbance associated with placing the RRDAP. Bats in the treatment group were exposed for 24 hours; the paste was removed, sealed and refrigerated. As with RRDAP placement in the treatment chamber, the door of the control chamber was sham opened and closed to emulate conditions of the treatment group when the RRDAP was removed. Bats were visually inspected via camera at 4 hour intervals for the first 24 hours to watch for visible behavioral response to the treatment. Starting day 2 through day 7, visual inspections were at 4 hour intervals between 0700 and 1900 and cameras were checked each morning to determine if bats displayed behavior indicating distress during the night.

On day 7 both chambers were opened to visually inspect, weigh and offer food to all bats and to replace water within chambers. An additional treatment was initiated for 24 hours starting on day 8 as no observable distress (no abnormalities of skin, mucous membranes, or respiration) were observed in either group. The 2 Pd positive bats from the toxicity assessment were included as a low Pd cohort (representing treatment at an early stage of infection) bringing total number of bats in the RRDAP48 treatment group to 10.

Bats were placed in mesh enclosures (n=2, 37×37×75 cm Apogee Reptarum™, Dallas, Tex., USA) by treatment group and each enclosure was placed in an environmental chamber (n=2 chambers; Geneva Scientific Model I-36NL, Fontana, Wis., USA). Each chamber was maintained at 10° C. for 24 hours to allow bats to recover from blood sampling; chambers were then lowered to 7° C. and treatment initiated.

Behaviors of each group were evaluated by viewing all recordings and assigning behaviors to categories (Table 8) and whether clusters were maintained during non-active periods. As in the toxicity assessments, activities were calculated as total times for each group per activity divided by number of bats in group per day of experiment and cumulative.

To confirm inhibition or eradication of viable mycelia within wing tissues of surviving bats and second season disease development without subsequent exposure to Pd, survivors were transferred from the hibernation chamber to a flight chamber (2 m×2 m×2.5 m) and received care. These bats were placed into a hibernation chamber to monitor for presence of Pd or development of disease.

RRDAP Treatment Trial: Necropsy, Histopathology, and Wing Scoring

All bats that died or were euthanized during the treatment trial underwent gross necropsy. Immediately after necropsy, the entire bat was fixed in 10% neutral buffered formalin. In order to determine if the exposure could have attributed to the cause of death, all internal organs except the reproductive tract were trimmed and embedded in preparation for hematoxylin and eosin (H&E) stain. One entire wing was chosen at random and removed from each bat. The wing membrane was trimmed into multiple rectangular strips and the cut surfaces were embedded for sectioning and staining Wing membranes were stained with periodic acid-Schiff stain (PAS) in addition to H&E to allow complete visualization of the fungus. H&E and PAS stained wing slides from each bat were scored blindly by a veterinary evaluator. Using a light microscope, slides were examined histologically for amount of Pd fungus and degree of hyphae invasion of the wings. Wing condition was scored from 0 (normal) to 4 (severe) using the scale in Table 9.

time-dependent covariates, ties were handled using the TIES=EXACT option in the PHREG procedure and likelihood ratio tests were computed. Survival and hazard functions were estimated with fixed (SEX, $C_T$ (categories), TRT) and time-dependent variables (WT, BCI, WS, DS, FD) using both the survival time notation and the counting process notation. For count notation, multiple records (with consecutive start and end times) for each individual were created to account for changes in the time-dependent variables when each mortality event occurred over the study period. Bat mortality was expressed as a failure event and surviving bats at each interval were expressed as censored data. A stepwise approach was used to sequentially remove non-significant variables if the resultant model had no significant change in the HR or AIC. Proportionality assumptions were checked with Schoenfelds's residuals and overall goodness of fit (GOF) evaluation. Models were compared using raw CT or relative initial Pd load (categories=low, medium or high CT) in order to control for any variation in the shape of the hazard function between

TABLE 9

Histologic severity scoring (SS) of white-nose syndrome (WNS) using wing membrane.

| Histologic Parameter | Score | Description |
| --- | --- | --- |
| Amount of Pd Fungus | 0 (normal) | No evidence of conidia and fungus |
|  | 1 (minimal) | Conidia present on wing surface, fungus present in 1-5 hair follicles without epithelial cell involvement, and/or 1-5 scattered colonies of conidia or fungal cupping lesions throughout wing. |
|  | 2 (mild) | At least one fungal cupping lesion and/or fungal hyphae present throughout wing in most 20x focal fields. |
|  | 3 (moderate) | At least two fungal cupping lesions and/or fungal hyphae in most 20x fields. |
|  | 4 (severe) | Fungal cupping lesions and fungal hyphae in all 20x fields |
| Degree of Hyphae Invasion | 0 (normal) | No evidence of conidia and fungus |
|  | 1 (minimal) | Fungus present on epidermis with no invasion into dermis |
|  | 2 (mild) | Fungus present on epidermis and penetrating into dermis |
|  | 3 (moderate) | Fungus present on epidermis and within dermis |
|  | 4 (severe) | Fungus penetrating entire cross section of wing |
| Inflammation | 0 (normal) | No inflammatory response present |
|  | 1 (minimal) | Few neutrophils throughout wing tissue, minimal edema may be present |
|  | 2 (mild) | Few neutrophils throughout wing tissue, with at least one focal area of neutrophils around a fungal cupping lesion or an area of dense fungal hyphae, mild edema may be present |
|  | 3 (moderate) | Many neutrophils throughout the wing tissue, with at least two focal areas of neutrophils around fungal cupping lesions, mild to moderate edema may be present |
|  | 4 (severe) | Many neutrophils throughout the wing tissue, multifocal areas of neutrophils around fungal cupping lesions, moderate to severe edema may be present |
| Necrosis | 0 (normal) | No necrosis present |
|  | 1 (minimal) | At least one area of necrosis present on wing and less than half of wing width affected |
|  | 2 (mild) | At least one area of necrosis present on wing and more than half of wing width affected |
|  | 3 (moderate) | At least one area of necrosis present on wing and the entire wing width affected |
|  | 4 (severe) | Multifocal areas of necrosis present on wing and the entire wing width affected |

Slides were prepared and stained by Idexx Bioresearch Histopathology Service (Columbia, Mo.).

RRDAP Treatment Trial: Analysis

Analyses were performed as in toxicity assessment in SAS (SAS® 9.3, SAS Institute Inc.). WT and BCI were modeled separately due to inherent correlation, (Pearson, r=0.91, p=<0.0001). Multivariate Cox proportional hazard models (CPHM) were fitted while accounting for covariates that could affect outcome (SWT, WS, DS, CT, (food consumption (FD)) using Cox regression adapted for analysis of amount of detectible conidia at trial onset. WT and BCI were modeled separately due to inherent correlation, (Pearson, r=0.90, p=<0.0001) and AIC of best model was compared to evaluate predictive ability. Analyses of overall survival (OS) were analyzed with non-parametric Kaplan-Meier curves and differences assessed by log-rank test (PROC LIFETEST).

Results 16 healthy and 18 naturally Pd infected *M. lucifugus* were studied in vivo under controlled conditions to evaluate the toxicity and efficacy of R. rhodochrous DAP 96253 for treatment of WNS. No evidence of toxicity was found in either group and a significant increase in survival in the WNS affected group was observed.

Toxicity Trials

Data (WT and BCI) were normally distributed on Day 1. Shapiro-Wilks test of Normal Distribution for bat weight (g) for bats included in Toxicity Assessment and Randomized Control Treatment Trial of induced *Rhodococcus rhodochrous* DAP 96253.

Toxicity Assessment

WT: NO RRDAP-low W=0.98 p=0.78 n=3, NO RRDAP-none W=0.89 p=0.35 n=5; RRDAP72-low W=1 p=1 n=2, RRDAP72-none W=0.84 p=0.13 n=6.

Treatment Trials

WT: NO RRDAP-high w=0.94 p=0.63 n=5; NO RRDAP-med w=0.83 p=0.19 n=3; RRDAP48-high w=0.90 p=0.35 n=6; RRDAP48-med w=1 p=1 n=2; RRDAP48-low w=1 p=1 n=2.

Figure 9:
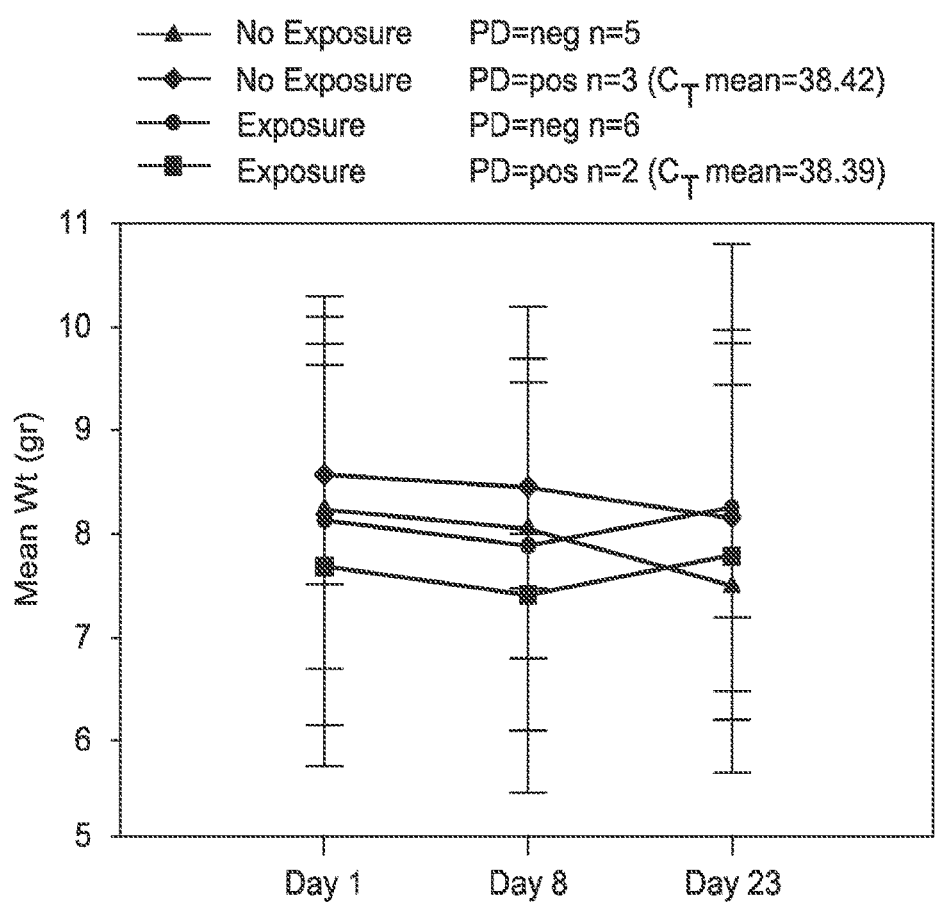
FIG. 9 is a plot showing mean body weight changes of bats exposed to *Rhodococcus* for 72 hours. WNS positive bats are separate from uninfected bats.
Figure 10:
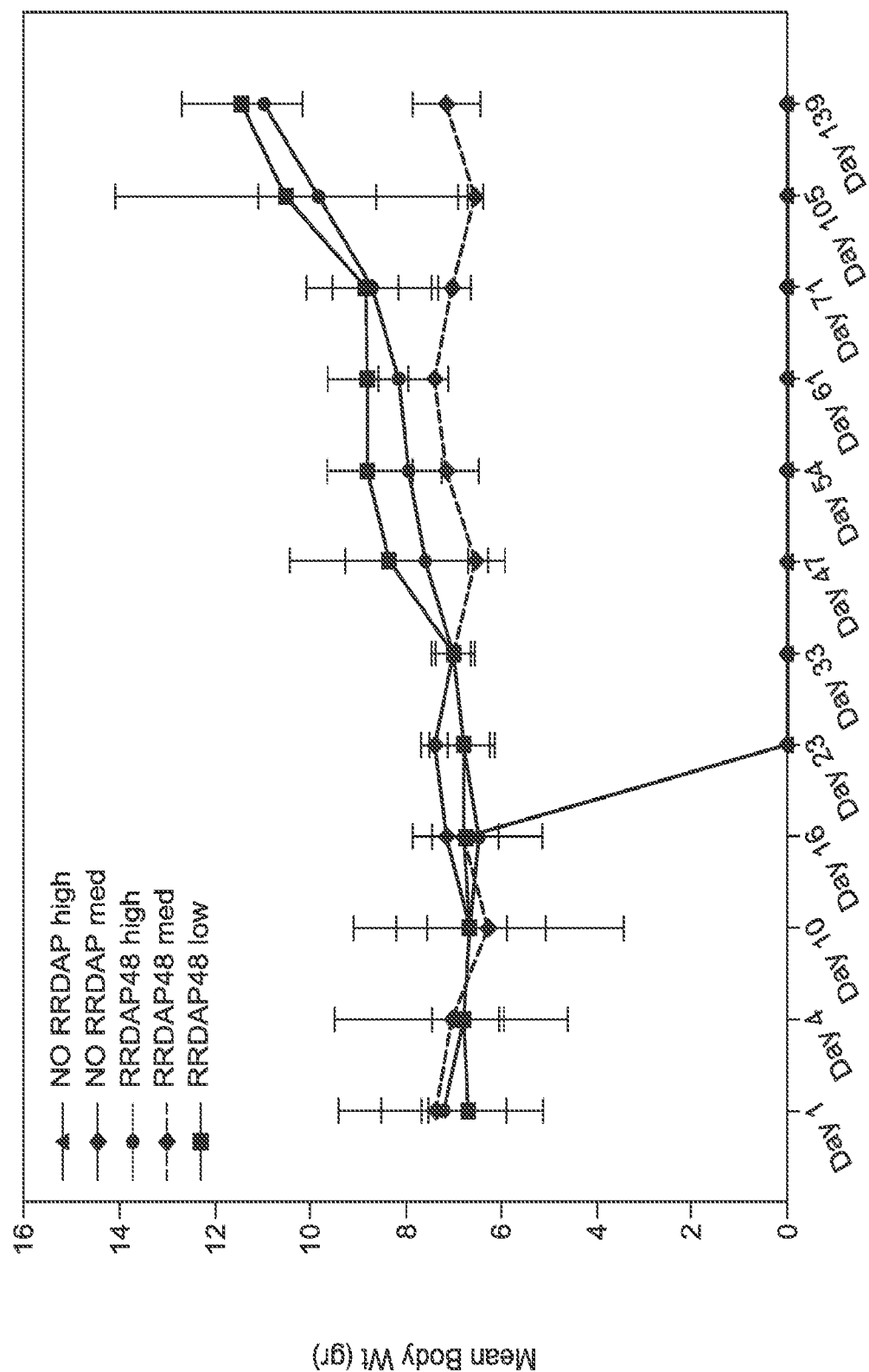
FIG. 10 is a plot showing body mass of WNS positive bats treated with *Rhodococcus* for 48 hours (RRDAP48) and untreated control. Body weights of "'0" indicate mortality.

Initial WT and BCI were generally lower for the RRDAP72 group but no significant differences ($\alpha=0.05$) were found for mean WT or BCI at Day 1, 8, or 26 between treatment groups and treatment group*Pd status (Tables 10-13; FIG. 9). WS, DS, and CT were not strongly correlated (highest correlation, Pearson, r=0.38, WS:CT). One bat from the NO RRDAP, Pd-status=neg, group died on Day 15, resulting in a single failure event; necropsy, results of culture, PCR and histopathology were all negative for WNS. In summary, the NO RRDAP group had 1 failure out of 8 (12.5%) and the RRDAP72 group had no failures out of 8 resulting in 93.5% of the of the total group being censored. This high level of censored data precluded assessment of the contribution of covariates and Hazard Ratio estimate. Cumulative survival at the end of the toxicity assessment was 0.88 and 1.00 (NO RRDAP and RRDAP72, respectively). No difference in survival was found between either treatment ($\chi2=1.39$, df=1, p=0.24) or treatment stratified by Pd status ($\chi2=1.58$, df=1, p=0.21). AIC values comparing stratified and unstratified forms of the model indicated the stratified model had slightly better fit (AIC values, 4.80 and 5.54, respectively) which may suggest Pd status had at least a minor influence on weight and body condition index.

TABLE 10

Mean body weight for bats included in toxicity assessment of induced *R. rhodochrous* DAP96253 for inhibition of *P. destructans* (Pd) by treatment groups.

| | | Day 1 | | | | Day 8 | | | | Day 26 | | | |
|---|---|---|---|---|---|---|---|---|---|---|---|---|---|
| Treatment | N | Mean Wt (g) | sd | F | p | Mean Wt (g) | sd | F | p | Mean Wt (g) | sd | F | p |
| NO RRDAP (Control) | 8 | 8.56 | 1.10 | 0.92 | 0.35 | 8.38 | 1.25 | 0.67 | 0.42 | 8.27 | 1.44 | 0.19 | 0.67 |
| RRDAP72 | 8 | 8.08 | 1.01 | | | 7.96 | 1.01 | | | 8.01 | 1.02 | | |

Standard deviation (sd),
F-test value,
p-value,
alpha = 0.05

TABLE 11

Mean body weight for bats included in toxicity assessment of induced *R. rhodochrous* DAP96253 for inhibition of *P. destructans* (Pd) by treatment groups and Pd status.

| | | Day 1 | | | | Day 8 | | | | Day 26 | | | |
|---|---|---|---|---|---|---|---|---|---|---|---|---|---|
| Treatment | N | Mean Wt (g) | sd | F | p | Mean Wt (g) | sd | F | p | Mean Wt (g) | sd | F | p |
| NO RRDAP PD = neg | 5 | 8.22 | 1.26 | 2.12 | 0.59 | 8.04 | 1.48 | 2.21 | 0.61 | 7.72* | 1.74 | 4.47 | 0.45 |
| NO RRDAP PD = pos | 3 | 9.13 | 0.50 | | | 8.96 | 0.50 | | | 9.00 | 0.50 | | |
| RRDAP72 PD = neg | 6 | 8.25 | 1.01 | 1.96 | 0.84 | 8.15 | 0.92 | 1.67 | 0.81 | 8.25 | 0.85 | 3.28 | 0.72 |
| RRDAP72 PD = pos | 2 | 7.60 | 0.99 | | | 7.40 | 0.30 | | | 7.30 | 1.20 | | |

Standard deviation (sd),
F-test value,
p-value,
alpha = 0.05;
*n = 4

TABLE 12

Mean body condition index for bats included in toxicity assessment of induced *R. rhodochrous* DAP96253 for inhibition of *P. destructans* (Pd) by treatment groups.

| | | Day 1 | | | | Day 8 | | | | Day 26 | | | |
|---|---|---|---|---|---|---|---|---|---|---|---|---|---|
| Treatment | N | Mean BCI | sd | F | p | Mean BCI | sd | F | p | Mean BCI | sd | F | p |
| NO RRDAP (Control) | 8 | 0.212 | 0.035 | 0.73 | 0.56 | 0.208 | 0.038 | 1.00 | 0.34 | 0.207 | 0.043 | 0.65 | 0.43 |
| RRDAP72 | 8 | 0.199 | 0.018 | | | 0.201 | 0.014 | | | 0.202 | 0.016 | | |

Standard deviation (sd),
F-test value,
p-value,
alpha = 0.05

TABLE 13

Mean body condition index for bats included in toxicity assessment induced *R. rhodochrous* DAP96253 for inhibition of *P. destructans* (Pd) by treatment groups and Pd status.

| | | Day 1 | | | | Day 8 | | | | Day 26 | | | |
|---|---|---|---|---|---|---|---|---|---|---|---|---|---|
| Treatment | N | Mean BCI | sd | F | p | Mean BCI | sd | F | p | Mean BCI | sd | F | p |
| NO RRDAP PD = neg | 5 | 0.203 | 0.042 | 1.47 | 0.62 | 0.190 | 0.047 | 0.66 | 0.65 | 0.194* | 0.056 | 0.72 | 0.62 |
| NO RRDAP PD = pos | 3 | 0.227 | 0.012 | | | 0.223 | 0.015 | | | 0.222 | 0.013 | | |
| RRDAP72 PD = neg | 6 | 0.203 | 0.018 | 0.90 | 0.95 | 0.204 | 0.014 | 0.24 | 0.92 | 0.207 | 0.016 | 1.92 | 0.87 |
| RRDAP72 PD = pos | 2 | 0.187 | 0.013 | | | 0.190 | 0.009 | | | 0.191 | 0.006 | | |

Standard deviation (sd),
F-test value,
p-value,
alpha = 0.05;
*n = 4.

Due to these bats being held for concurrent studies, they were not euthanized to evaluate histological differences in skin and organ tissues. However, after both groups were placed in the single chamber for holding until spring, 2 additional bats from each treatment group died and tissues from all major organs and wings were evaluated for potential differences between the control group and those exposed to induced cells of *R. rhodochrous* DAP 96253.

On gross necropsy, each bat was noted to have minimal visceral and subcutaneous adipose tissue. On histopathological examination, bats did not exhibit evidence of fungal invasion of wings; however, two bats had multifocal areas of Pd conidia present along the epidermis. None of the mortality observed in these bats appeared to be related to exposure.

Treatment Trials

Data (WT and BCI) were normally distributed on Day 1. WS, DS and CT were not strongly correlated (highest correlation, r=0.55, (WS:DS)). There were no significant differences ($\alpha$=0.05) in mean WT, BCI, WS, or DS at Day 1, 10, 16, 23 between treatment groups and treatment group by $C_T$ (Tables 14-15, FIG. 10). Survival models were evaluated with 2 approaches, the first included raw $C_T$ values as a covariate and the second included categories of low, medium or high $C_T$ values to stratify the data set. By either approach, cumulative survival was greater for the RRDAP48 treatment group than the NO RRDAP group (0.0 and 0.6; NO RRDAP and RRDAP48, respectively) (FIG. 11). Tests of nonzero slope of the scaled Schoenfeld residuals on time indicated proportional hazard criteria were met. By Day 23, no individual survived from the NO RRDAP group so survival curves are compared for this period even though 6 bats from the RRDAP48 group are alive to date.

TABLE 14

Mean body weight for bats included in toxicity assessment of induced *R. rhodochrous* DAP96253 for inhibition of *P. destructans* (Pd) by treatment groups.

| | | Day 1 | | | | Day 8 | | | | Day 26 | | | |
|---|---|---|---|---|---|---|---|---|---|---|---|---|---|
| Treatment | N | Mean Wt (g) | sd | F | p | Mean Wt (g) | sd | F | p | Mean Wt (g) | sd | F | p |
| NO RRDAP (Control) | 8 | 8.56 | 1.10 | 0.92 | 0.35 | 8.38 | 1.25 | 0.67 | 0.42 | 8.27 | 1.44 | 0.19 | 0.67 |
| RRDAP72 | 8 | 8.08 | 1.01 | | | 7.96 | 1.01 | | | 8.01 | 1.02 | | |

Standard deviation (sd),
F-test value,
p-value,
alpha = 0.05

TABLE 15

Mean body weight for bats included in toxicity assessment of induced *R. rhodochrous* DAP96253 for inhibition of *P. destructans* (Pd) by treatment groups and Pd status.

| | | Day 1 | | | | Day 8 | | | | Day 26 | | | |
|---|---|---|---|---|---|---|---|---|---|---|---|---|---|
| Treatment | N | Mean Wt (g) | sd | F | p | Mean Wt (g) | sd | F | p | Mean Wt (g) | sd | F | p |
| NO RRDAP PD = neg | 5 | 8.22 | 1.26 | 2.12 | 0.59 | 8.04 | 1.48 | 2.21 | 0.61 | 7.72* | 1.74 | 4.47 | 0.45 |
| NO RRDAP PD = pos | 3 | 9.13 | 0.50 | | | 8.96 | 0.50 | | | 9.00 | 0.50 | | |
| RRDAP72 PD = neg | 6 | 8.25 | 1.01 | 1.96 | 0.84 | 8.15 | 0.92 | 1.67 | 0.81 | 8.25 | 0.85 | 3.28 | 0.72 |
| RRDAP72 PD = pos | 2 | 7.60 | 0.99 | | | 7.40 | 0.30 | | | 7.30 | 1.20 | | |

Standard deviation (sd),
F-test value,
p-value,
alpha = 0.05;
*n = 4.

TABLE 16

Mean body condition index for bats included in toxicity assessment of induced *R. rhodochrous* DAP96253 for inhibition of *P. destructans* (Pd) by treatment groups.

| | | Day 1 | | | | Day 8 | | | | Day 26 | | | |
|---|---|---|---|---|---|---|---|---|---|---|---|---|---|
| Treatment | N | Mean BCI | sd | F | p | Mean BCI | sd | F | p | Mean BCI | sd | F | p |
| NO RRDAP (Control) | 8 | 0.212 | 0.035 | 0.73 | 0.56 | 0.208 | 0.038 | 1.00 | 0.34 | 0.207 | 0.043 | 0.65 | 0.43 |
| RRDAP72 | 8 | 0.199 | 0.018 | | | 0.201 | 0.014 | | | 0.202 | 0.016 | | |

Standard deviation (sd),
F-test value,
p-value,
alpha = 0.05

TABLE 17

Mean body condition index for bats included in toxicity assessment induced *R. rhodochrous* DAP96253 for inhibition of *P. destructans* (Pd) by treatment groups and Pd status.

| Treatment | N | Day 1 Mean BCI | sd | F | p | Day 8 Mean BCI | sd | F | p | Day 26 Mean BCI | sd | F | p |
|---|---|---|---|---|---|---|---|---|---|---|---|---|---|
| NO RRDAP PD = neg | 5 | 0.203 | 0.042 | 1.47 | 0.62 | 0.190 | 0.047 | 0.66 | 0.65 | 0.194* | 0.056 | 0.72 | 0.62 |
| NO RRDAP PD = pos | 3 | 0.227 | 0.012 | | | 0.223 | 0.015 | | | 0.222 | 0.013 | | |
| RRDAP72 PD = neg | 6 | 0.203 | 0.018 | 0.90 | 0.95 | 0.204 | 0.014 | 0.24 | 0.92 | 0.207 | 0.016 | 1.92 | 0.87 |
| RRDAP72 PD = pos | 2 | 0.187 | 0.013 | | | 0.190 | 0.009 | | | 0.191 | 0.006 | | |

Standard deviation (sd),
F-test value,
p-value,
alpha = 0.05;
*n = 4.

TABLE 18

Day 1 Mean Wt by Sex

| Effect | DF | F Value | Pr > F |
|---|---|---|---|
| SEX | 1 | 0.56 | 0.47 |
| SEX*$C_T$ | 2 | 0.20 | 0.66 |
| TRT*SEX | 1 | 2.26 | 0.16 |

TABLE 19

Day 1 WT

| Effect | DF | F Value | Pr > F |
|---|---|---|---|
| TRT | 1 | 0.18 | 0.68 |
| CT | 2 | 0.23 | 0.64 |
| TRT*CT | 1 | 2.98 | 0.12 |

TABLE 20

Day 1 BCI

| Effect | DF | F Value | Pr > F |
|---|---|---|---|
| TRT | 1 | 0.08 | 0.79 |
| CT | 2 | 0.48 | 0.50 |
| TRT*CT | 1 | 0.02 | 0.89 |

TABLE 21

Day 1 Wingscore and Dehydration Score

| Source | DF | F Value | Pr > F |
|---|---|---|---|
| WINGSCORE | 1 | 0.38 | 0.55 |
| DEHYSCORE | 1 | 0.84 | 0.37 |
| WINGSCORE*DEHYSCORE | 1 | 0.47 | 0.50 |

TABLE 22

Day 1 Mean WT by TRT*CT

| TRT | CT | WT MEAN | MEAN Number |
|---|---|---|---|
| NO_RRDAP | high | 7.28 | 1 |
| NO_RRDAP | med | 7.17 | 2 |
| RRDAP48 | high | 7.47 | 3 |
| RRDAP48 | low | 6.70 | 4 |
| RRDAP48 | med | 7.60 | 5 |

Means for effect TRT*CT
H0: Mean (i) = Mean (j)

| i | j 1 | 2 | 3 | 4 | 5 |
|---|---|---|---|---|---|
| 1 | | 0.9996 | 0.9937 | 0.8881 | 0.9857 |
| 2 | 0.9996 | | 0.9791 | 0.9593 | 0.9687 |
| 3 | 0.9937 | 0.9791 | | 0.7339 | 0.9995 |
| 4 | 0.8881 | 0.9593 | 0.7339 | | 0.7616 |
| 5 | 0.9857 | 0.9687 | 0.9995 | 0.7616 | |

Gross necropsy (NO RRDAP n=8; RRDAP48 n=4) revealed minimal subcutaneous and visceral adipose tissue which is consistent with the reduced fat stores observed in WNS affected bats. On histopathological examination of bats, NO RRDAP bats had a mean score of 4.00±0 sd (n=4) for amount of Pd fungus present throughout the wing membrane and a mean score of 3.25±0.96 for degree of hyphae fungal invasion. The RRDAP48 bats had a mean score of 2.67±0.58 sd (n=3) for amount of fungus present throughout the wing membrane and a mean score of 2.27±0.58 for degree of hyphae fungal invasion.

In order to elucidate whether *R. rhodochrous* DAP 96253 volatiles provide a safe, non-contact treatment option to increase survival of bats naturally infected with Pd, in vivo trials were conducted to assess potential toxicity to healthy *M. lucifugus* and randomized control trials (RCT) to assess efficacy of treatment in bats with WNS. Results from the toxicity assessments indicates that induced *R. rhodochrous* DAP 96253 had no effect on healthy bats. No aberrant behaviors indicating irritation to eyes or mucous membranes were observed during or after exposure to RRDAP. Overall survival did not differ between exposed bats and those not exposed in this toxicological assessment. Behavior observed in both groups were consistent with normal torpid behavior of bats held in hibernation chambers at low ambient temperatures. Bats were primarily torpid but did arouse between torpor bouts and exhibited species typical behaviors including grooming, flying, crawling, and drinking. Similar behaviors have been reported during infection trials for WNS-affected and WNS-unaffected bats.

While time observed in active behaviors differed somewhat between the 2 groups, the differences in total time spent active and time drinking were not significant. However, the NO RRDAP group spent significantly more time in grooming and eating behavior than did the RRDAP72 group. Weight decline was similar among all bats until approximately Day 8 post exposure (FIG. 9). However, WT and BCI of the NO RRDAP group continued to decline over the length of the experiment while bats in the RRDAP72 group began increasing in WT and BCI following evaluations on Day 8. While changes in Pd loads were not analyzed in this trial, it is possible that the 3 individuals with low positive spore loads could have transmitted conidia to other individuals in this group and 1 or more of bats in this group could potentially have been exhibiting subclinical effects of Pd infection. Histopathological examination of wing tissue of 2 individuals from this group revealed one small area of conidia on the epidermal surface of the wings; however, histologic evaluation did not reveal mycelial invasion of tissues.

Figure 11:
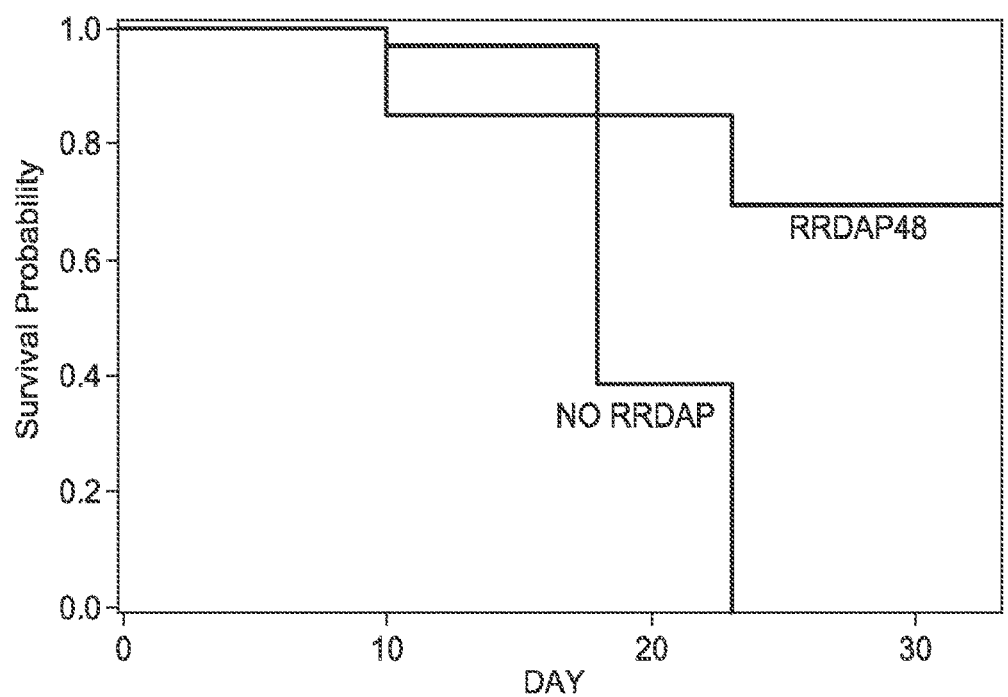
FIG. 11 is a graph showing survival probability over time for infected *M. lucifugus* treated (RRDAP48) or not treated (NO RRDAP) with *R. rhodochrous* DAP96253.

Results from the treatment trials show that exposure to induced R. rhodochrous DAP96253 shared airspace reduced the mortality of naturally WNS infected M. lucifugus and improve survival (0% NO RRDAP, 60% RRDAP48) (FIG. 11).

Figure 12:
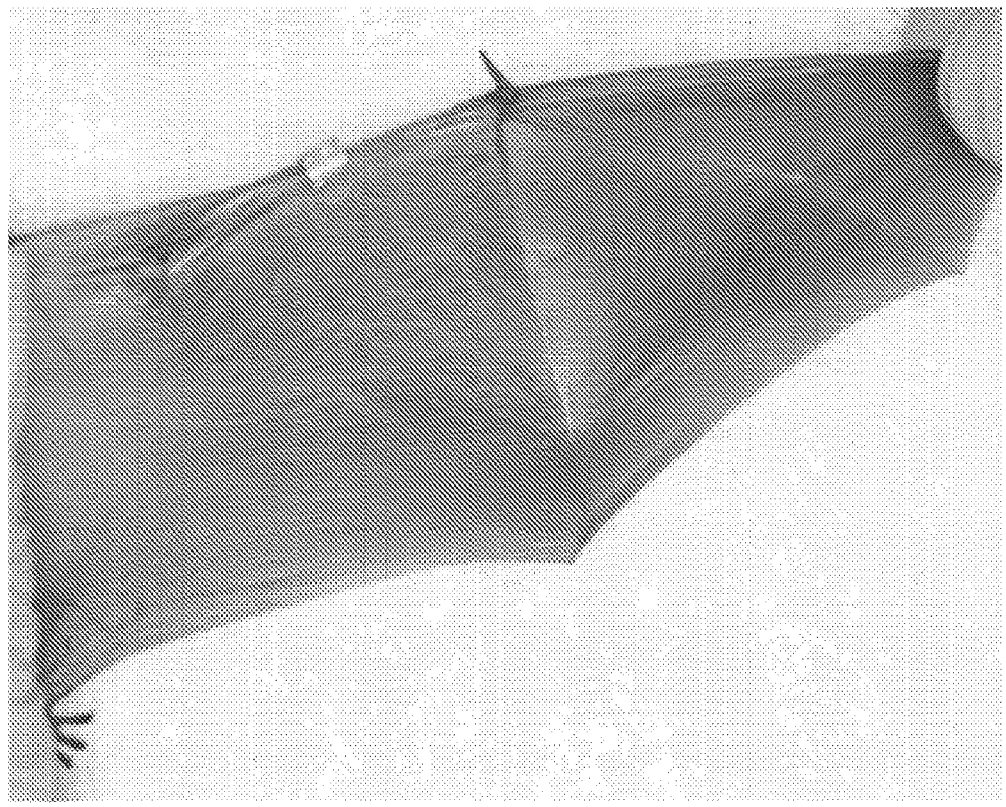
FIG. 12 is a gross pathology image of a wing from bat not treated with *R. rhodochrous* on Day 7.

Gross pathology of the NO RRDAP treatment group indicated minimal visual evidence of infection without assistance of UV light or histology (FIG. 12). However, all NO RRDAP bats presented with progressive clinical physiological symptoms of disease including lethargy, dehydration, inability to thermoregulate to euthermic temperature when handled for assessment, pale mucus membranes, reduced ability to swallow and general malaise leading to moribund condition and death. These symptoms are consistent with any of the currently hypothesized modes of mortality including dehydration, starvation, electrolyte imbalance and acid-base imbalances. All individuals in this group died prior to development of visual gross pathology of wing lesions.

Figure 13:
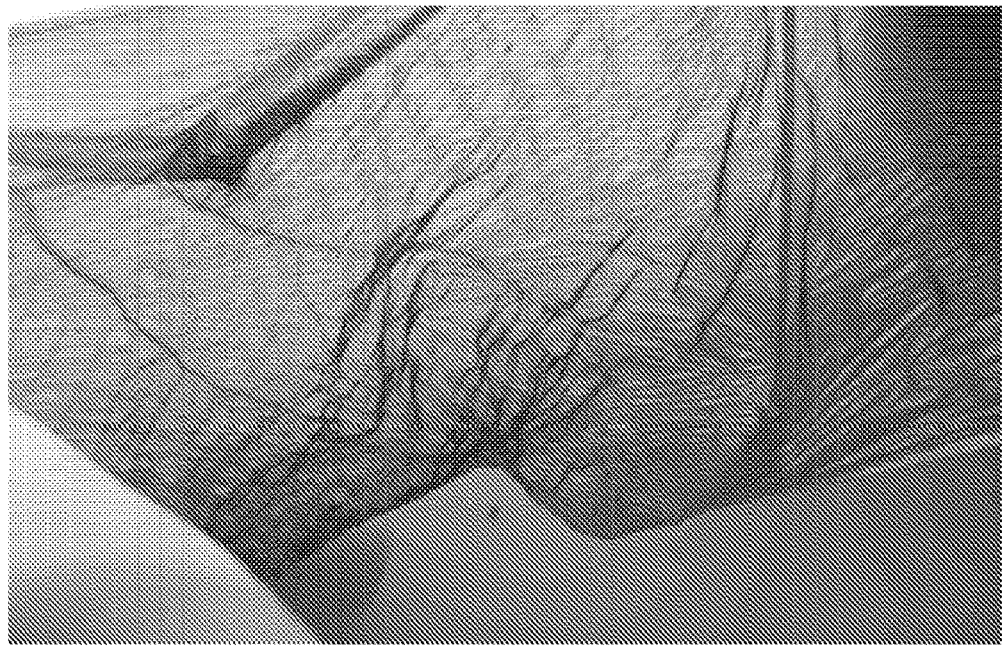
FIG. 13 is a gross pathology image of a wing from bat treated with *R. rhodochrous* on Day 20 showing reduced lesion and scar tissue formation.

In RRDAP48 treated bats, disease progression of symptoms associated with clinical physiological disruption were less severe. However, starting approximately Day 10, wing tissues began to visually suggest cellular contraction, dehydration and associated self-adherence of tissue consistent with descriptions of post emergence pathology even though their torpor bouts trended longer and arousal duration trended lower than the untreated group. Wing lesions associated with disease progression while RRDAP48 bats were maintained at 7° C. were characteristically either stellate or linear areas of wing membrane that resembled dense tissue when back-lit (FIG. 13).

Wings appeared to lose elasticity and tensile strength, became dry and were susceptible to tearing, suggesting the initiation of an inflammatory response even while bats were maintaining torpid body temperatures and behavior. Additionally, histopathological findings of bats from this group included mild multi-focal accumulations of neutrophils present in the vessel lumen of the liver, lungs, heart and wing. Interestingly, the majority of the neutrophils observed in the wing, were intraluminal or perivascular, and were not surrounding the fungal cupping lesions. This provides additional evidence of a systemic inflammatory response, even at lower body temperatures.

Hibernation is characterized by intervals of torpor ranging in duration from a few days to weeks. Basal metabolic rate during torpor represents <5% of normal rates and basal temperature ($T_b$) is maintained within a few degrees above ambient temperatures ($T_a$) (Carey et al. 2004). Torpor is interrupted by periods of arousal with intense metabolic activity. During hibernation, many physiological functions are effectively halted while a few proceed at greatly reduced rates. While considerable information detailing various aspects of the morphological, physiological, and biochemical changes that are associated with hibernation is available for some mammals, the cellular and molecular bases are still poorly understood. Currently, very little is known about the immune system of bats; either during hibernation or euthermic periods. Recent studies indicate the innate immune cell function is altered in torpid animals, it remains unknown whether innate sensing pathways, cytokine production, cell recruitment or other aspects of innate immune cell function are affected.

The treated bats maintained torpor for longer intervals and displayed more typical clustering behavior than the untreated bats yet they initiated an immune response within two weeks of treatment. This suggests additional biochemical mechanisms may be involved in the interactions between bats and Pd. There may be two possible explanations for this response: (a) killing the fungal conidia on the body surfaces and disruption of mycelial growth (lysis of fungal cell walls) within their wing tissues created increased signaling to their suppressed immune system, or (b) some mechanism (perhaps pattern recognition receptors (PRR) and pathogen associated molecular patterns (PAMP)) utilized by Pd to evade recognition by the bat's immune system was disrupted allowing them to recognize the pathogen. Since the objectives were to assess survivorship, these hypotheses were not evaluated.

Figure 14:
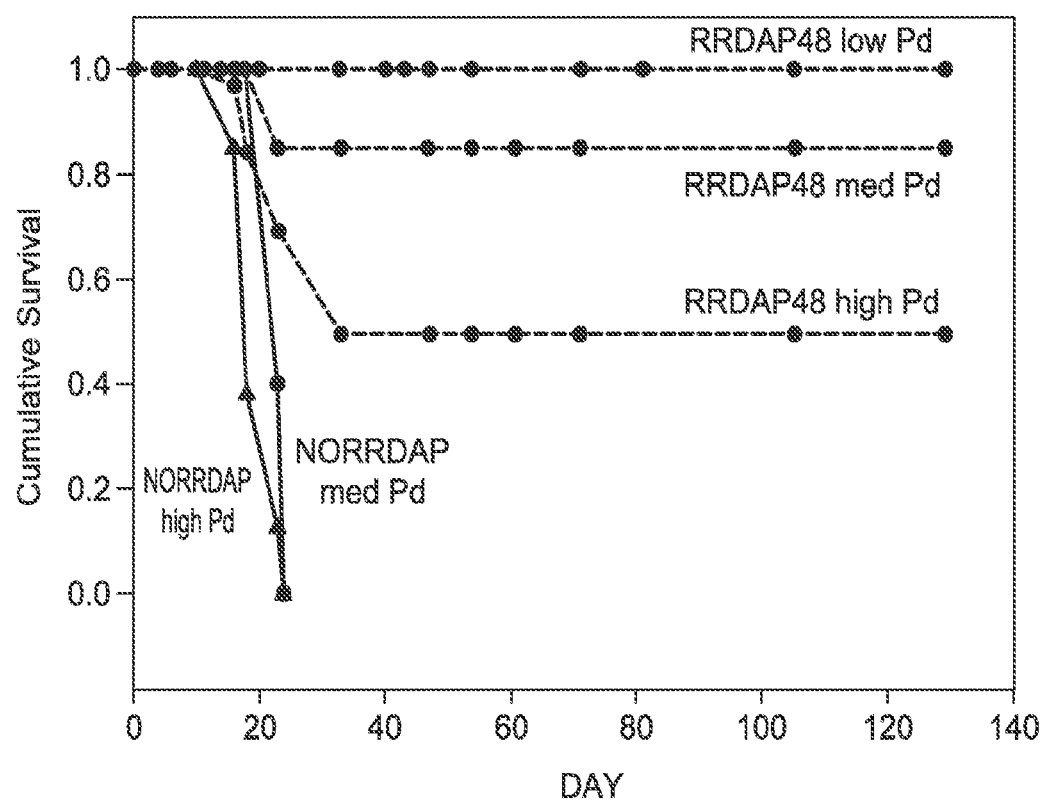
FIG. 14 is a graph showing cumulative survival of the treatment and control groups, segregated by infection severity, over the entire course of the trial.

Recent evidence indicates Pd load remains very low on all species during summer and early autumn with significant increases coinciding with increased periods of torpor and Pd loads peaking at the end of hibernation. Induced R. rhodochrous have been shown to be very effective in killing conidia, and since the bats with low conidia loads at experiment onset never developed evidence of fungal invasion of tissue, the preventative qualities of induced cells of R. rhodochrous DAP 96253 are demonstrated. Furthermore, the efficacy of treating WNS is further established. Earliest trials with R. rhodochrous in this study were on bats not clinically infected with the pathogen to assess whether the treatment was safe for use with bats. This resulted in bats used in treatment trials having additional time for disease progression and therefore, a more advanced stage of disease (evidenced by fluorescing wing tissues) and homeostasis disruptions that were already initiated. However, even with clinical disease and its related impacts at study onset, a significant improvement in survival for bats in shared airspace with R. rhodochrous DAP 96253 was shown. The disclosed results suggest improved survival in bats with lowest initial conidial load or lower levels of tissue invasion (FIG. 14). Therefore, treatment prior to fungal wing invasion offers highest opportunity to increase survival.

The rapid spread of Pd through eastern hibernacula allows little time for bats to adapt physiologically or to find more favorable hibernation sites. WNS driven declines towards extinction will likely continue for highly affected bat species unless populations can adapt fast enough to counter the rate of decline; essentially it becomes a race between demography and adaptive response. Bats treated with *R. rhodochrous* volatiles suggest a gain in advantage over the pathogen, which may provide the critical time needed to survive during a single hibernation period. This may, in turn, provide bats additional time to develop resistance or tolerance to Pd.

The results presented above serve as the first example of a treatment reducing the mortality of Pd infected bats in vivo and represents a major milestone in the development of tools to combat this wildlife epidemic. The successful implementation of an integrated disease management (IDM) system requires numerous and diverse methods of control, targeting specific features and phases of the disease cycle to obtain synergistic benefits. IDM has been used with tremendous success in the management of fungal pathogens in agriculture such as toxigenic *Aspergillus flavus* in peanuts as well as plant pathogenic fungi in hydroponic systems. The identification and validation of the antagonistic capacity of induced *R. rhodochrous* DAP 96253 facilitates the development of similar approaches in the management of WNS in bats. While complete mitigation of the development of WNS in bats is unlikely due to the vast geographic distribution of Pd as well as its ability to survive in host-free environments, a recent model suggests that moderate increases in survivorship may have a long-term beneficial impact to susceptible species. Accordingly the increase in survivorship presented in this manuscript indicates the potential of this control agent to have a significant impact on the survival of imperiled species and prevent the regional extirpation predicted if WNS remains unmitigated.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating or preventing fungal infection in an animal subject, comprising placing a composition comprising one or more bacteria in the proximity of, but not directly on, the subject, wherein the one or more bacteria are selected from the group consisting of *Rhodococcus rhodochrous* DAP 96253, *Rhodococcus rhodochrous* DAP 96622, *Rhodococcus erythropolis*, and combinations thereof, and wherein the one or more bacteria are provided in a quantity sufficient to inhibit or reduce fungal growth in the subject.

2. The method of claim 1, wherein the one or more bacteria are induced to produce one or more enzymes selected from the group consisting of nitrile hydratases, amidases, asparaginases, ACC deaminases, monooxygenases, dioxygenases, cyanidases, and combinations thereof.

3. The method of claim 2, wherein the composition further comprises the one or more enzymes produced by the one or more bacteria.

4. The method of claim 3, wherein the composition further comprises one or more cofactors for the one or more enzymes.

5. The method of claim 1, wherein the composition further comprises an inducing agent selected from the group consisting of urea, methyl carbamate, methacrylamide, acetamide, cobalt, asparagine, anhydrous asparagine, asparagine monohydrate, and combinations thereof.

6. The method of claim 5, wherein the inducing agent comprises urea or methyl carbamate and one or more of cobalt and asparagine.

7. The method of claim 1, wherein the composition further comprises a stabilizing agent.

8. The method of claim 7, wherein the stabilizing agent is trehalose.

9. The method of claim 1, wherein the one or more bacteria are fixed with glutaraldehyde and cross-linked.

10. The method of claim 1, wherein the one or more bacteria are provided in a coating layer.

11. The method of claim 10, wherein the coating layer is selected from a hydrophobic fatty acid polyester coating or a wax.

12. The method of claim 1, wherein the composition is provided in a liquid carrier, solid carrier, aerosol, or gel.

13. The method of claim 1, wherein the subject is a bat, wherein the fungal infection comprises *Pseudogymnoascus destructans*.

14. The method of claim 13, wherein the composition is applied to areas in or around a bat roost.

15. The method of claim 13, wherein the composition is provided in a bat lure.

16. The method of claim 1, wherein the subject is a honey bee, wherein the fungal infection is selected from the group consisting of *Ascosphaera apis, Nosema apis, Aspergillus fumigatus, Aspergillus flavus*, and *Aspergillus niger*.

17. The method of claim 16, wherein the composition is provided in a bait particle.

18. The method of claim 16, wherein the composition is provided in a wax.

19. The method of claim 18, wherein the wax is incorporated into a bee hive.

20. The method of claim 16, wherein the composition is provided in a powder.

21. The method of claim 20, wherein the powder is mixed with powdered sugar and applied as a dust to a bee hive.

22. The method of claim 16, wherein the composition is incorporated into a material at an entrance to a bee hive.

* * * * *